(12) United States Patent
Ito et al.

(10) Patent No.: US 12,296,339 B2
(45) Date of Patent: May 13, 2025

(54) MICROPARTICLE SORTING DEVICE, CELL THERAPEUTIC AGENT MANUFACTURING DEVICE, MICROPARTICLE SORTING METHOD AND PROGRAM

(71) Applicant: Sony Corporation, Tokyo (JP)

(72) Inventors: Tatsumi Ito, Kanagawa (JP); Gakuji Hashimoto, Kanagawa (JP); Kazuya Takahashi, Kanagawa (JP); Hirotaka Yoshida, Kanagawa (JP); Yasunobu Kato, Kanagawa (JP)

(73) Assignee: Sony Corporation, Tokyo (JP)

( * ) Notice: Subject to any disclaimer, the term of this patent is extended or adjusted under 35 U.S.C. 154(b) by 1107 days.

(21) Appl. No.: 17/273,277

(22) PCT Filed: Sep. 10, 2019

(86) PCT No.: PCT/JP2019/035591
§ 371 (c)(1),
(2) Date: Mar. 3, 2021

(87) PCT Pub. No.: WO2020/054735
PCT Pub. Date: Mar. 19, 2020

(65) Prior Publication Data
US 2021/0331172 A1 Oct. 28, 2021

(30) Foreign Application Priority Data

Sep. 10, 2018 (JP) ................... 2018-168711
Sep. 5, 2019 (JP) ................... 2019-161868

(51) Int. Cl.
B01L 3/00 (2006.01)
A61K 35/14 (2015.01)
C12Q 1/24 (2006.01)

(52) U.S. Cl.
CPC ........ *B01L 3/502761* (2013.01); *A61K 35/14* (2013.01); *B01L 3/502776* (2013.01);
(Continued)

(58) Field of Classification Search
CPC ......... B01L 3/502761; B01L 3/502776; B01L 2200/0652; B01L 2300/0654;
(Continued)

(56) References Cited

U.S. PATENT DOCUMENTS 9,789,485 B2 * 10/2017 Han ................... B01L 3/50273
2002/0005354 A1 1/2002 Spence
(Continued)

FOREIGN PATENT DOCUMENTS

CA 2752247 A1 10/2004
CN 101738357 A 6/2010
(Continued)

OTHER PUBLICATIONS

International Search Report and Written Opinion mailed Nov. 18, 2019 in connection with International Application No. PCT/JP2019/035591.

*Primary Examiner* — Michael McCullough
*Assistant Examiner* — Kalyanavenkateshware Kumar
(74) *Attorney, Agent, or Firm* — Wolf, Greenfield & Sacks, P.C.

(57) ABSTRACT

Provided is a technology for preparing a mixture including multiple types of microparticles in accordance with a predetermined ratio. The present technology provides a microparticle sorting device (100) including a control unit (103) comprising a determination unit that determines whether microparticles are sorted, on the basis of light generated by irradiating, with light, the microparticles flowing through a flow channel (155), in which the determination unit performs a primary sorting determination to determine,
(Continued)

on the basis of characteristics of the light generated, whether the microparticles belong to any one of two or more different microparticle populations, and then performs a secondary sorting determination to determine whether the microparticles determined to belong to any one of the microparticle populations in the primary sorting determination are sorted, on the basis of the particle constituent ratio specified for the two or more different microparticle populations. This technology may be used to prepare a cell therapeutic agent comprising a mixture of cells of different types in a predefined ratio, e.g. a mixture of various types of CAR T-cells showing a synergistic anti-tumor activity.

23 Claims, 7 Drawing Sheets

(52) U.S. Cl.
CPC ........ *C12Q 1/24* (2013.01); *B01L 2200/0652* (2013.01); *B01L 2300/0654* (2013.01); *B01L 2300/0816* (2013.01); *B01L 2300/0864* (2013.01); *B01L 2300/0867* (2013.01); *B01L 2400/049* (2013.01)

(58) Field of Classification Search
CPC ..... B01L 2300/0816; B01L 2300/0864; B01L 2300/0867; B01L 2400/049; G01N 15/149; G01N 15/1459; G01N 15/1484; G01N 2015/1006

See application file for complete search history.

(56) References Cited

U.S. PATENT DOCUMENTS

| | | |
|---|---|---|
| 2005/0112541 A1 | 5/2005 | Durack |
| 2008/0213821 A1 | 9/2008 | Liu et al. |
| 2008/0255705 A1 | 10/2008 | Degeal et al. |
| 2010/0123457 A1 | 5/2010 | Shinoda |
| 2012/0122084 A1 | 5/2012 | Wagner |
| 2012/0288920 A1 | 11/2012 | Takeda |
| 2014/0299522 A1 | 10/2014 | Ito |
| 2016/0061711 A1 | 3/2016 | Deka |
| 2016/0266027 A1 | 9/2016 | Muraki |
| 2018/0202916 A1 | 7/2018 | Lo et al. |

FOREIGN PATENT DOCUMENTS

| | | |
|---|---|---|
| CN | 103586221 A | 2/2014 |
| JP | 2010151777 A | 7/2010 |
| JP | 2011257241 A | 12/2011 |

* cited by examiner

[Fig. 1]
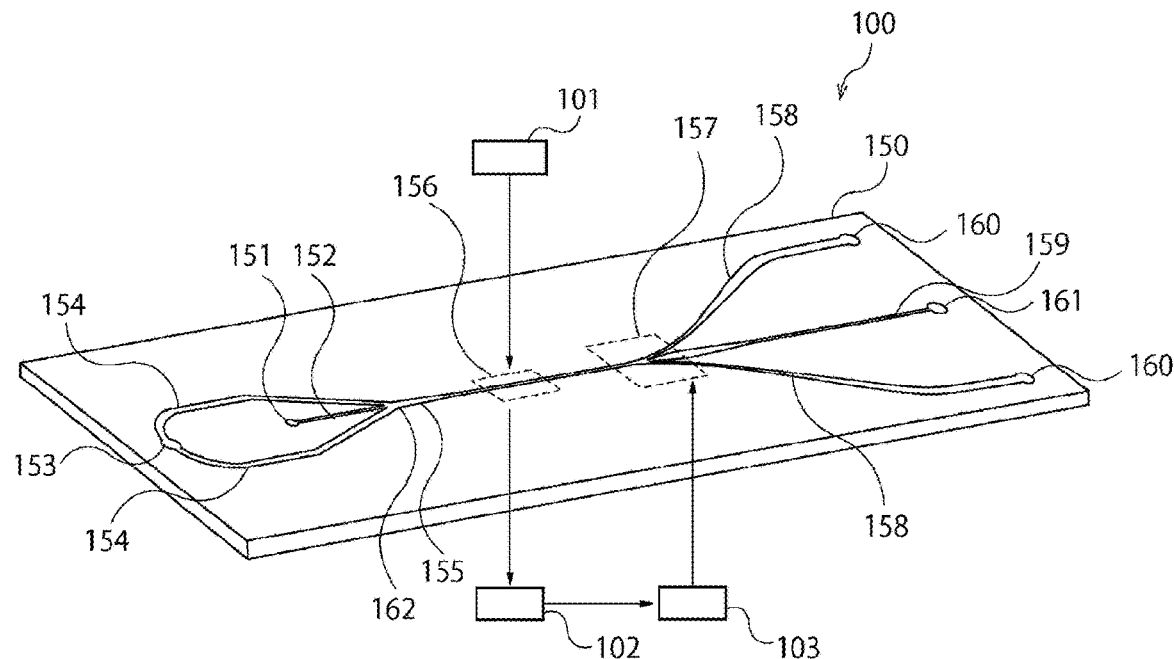
[Fig. 2]
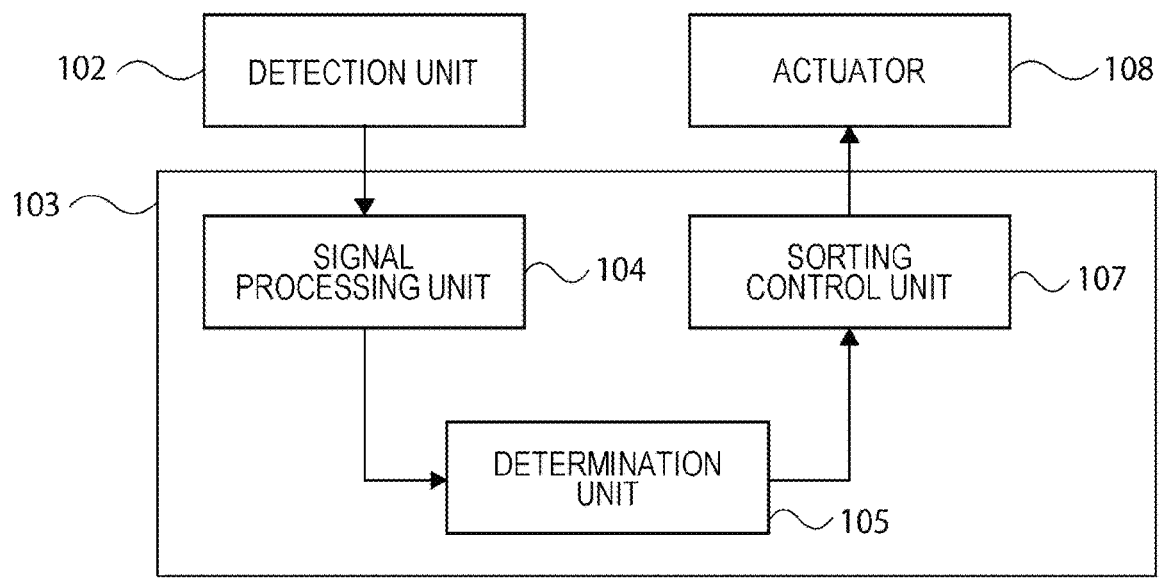

| GATE No. | GATE LOGIC | RATIO [%] | COMMENT |
|---|---|---|---|
| 1 | A & B & C | 50 | CD4+ |
| 2 | A & B & D | 50 | CD8+ |

[Fig. 6]
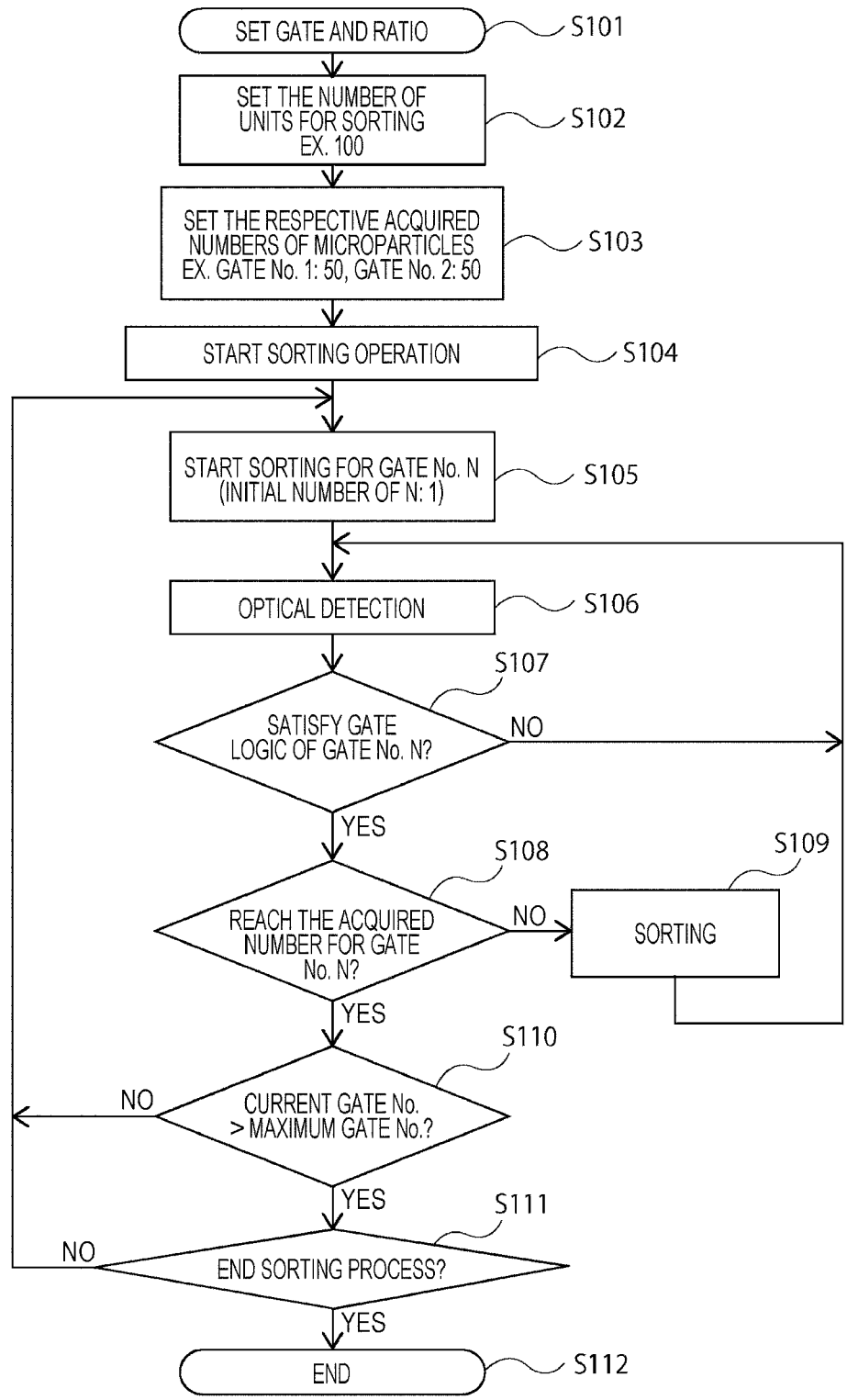

[Fig. 7]
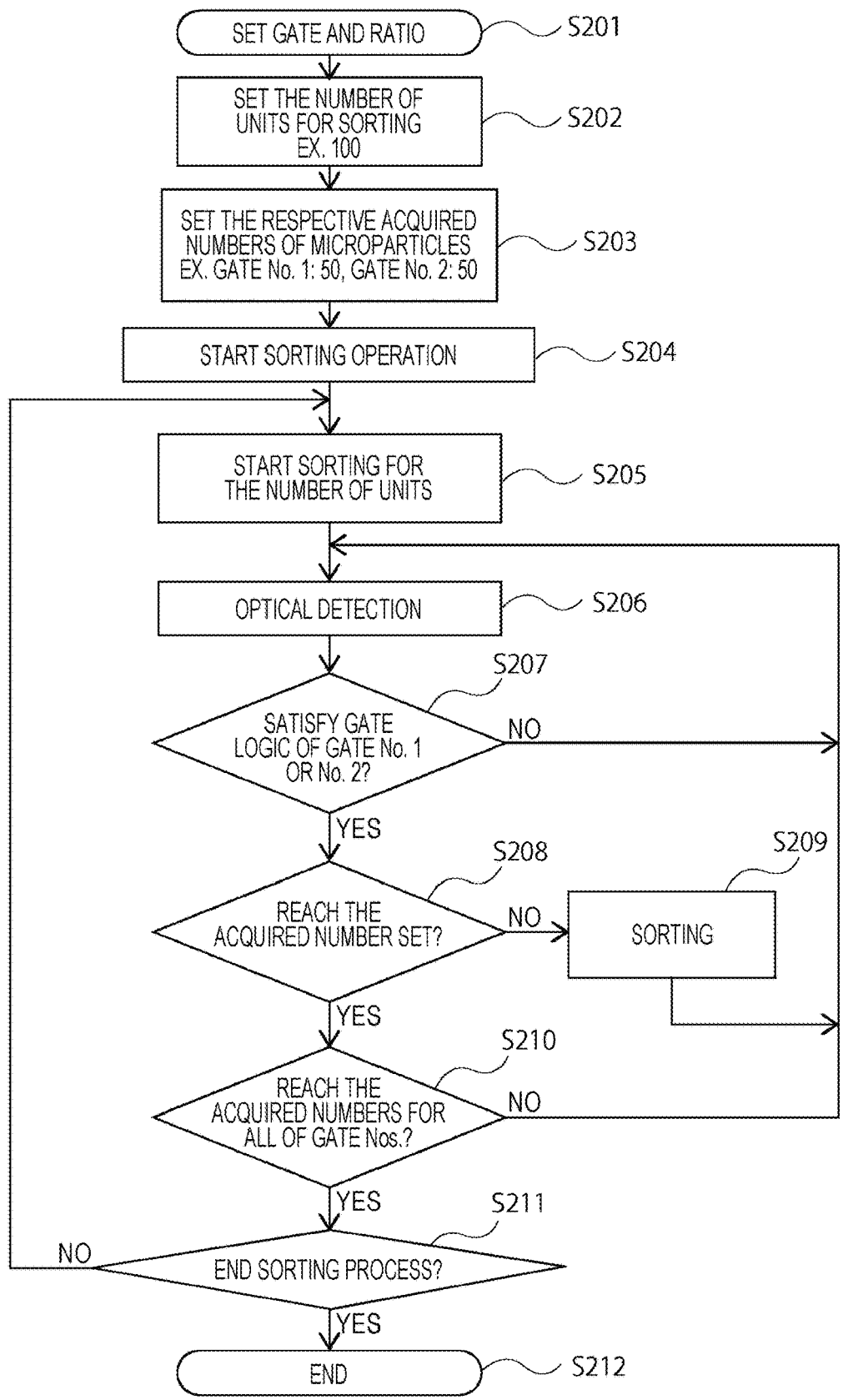

[Fig. 8]
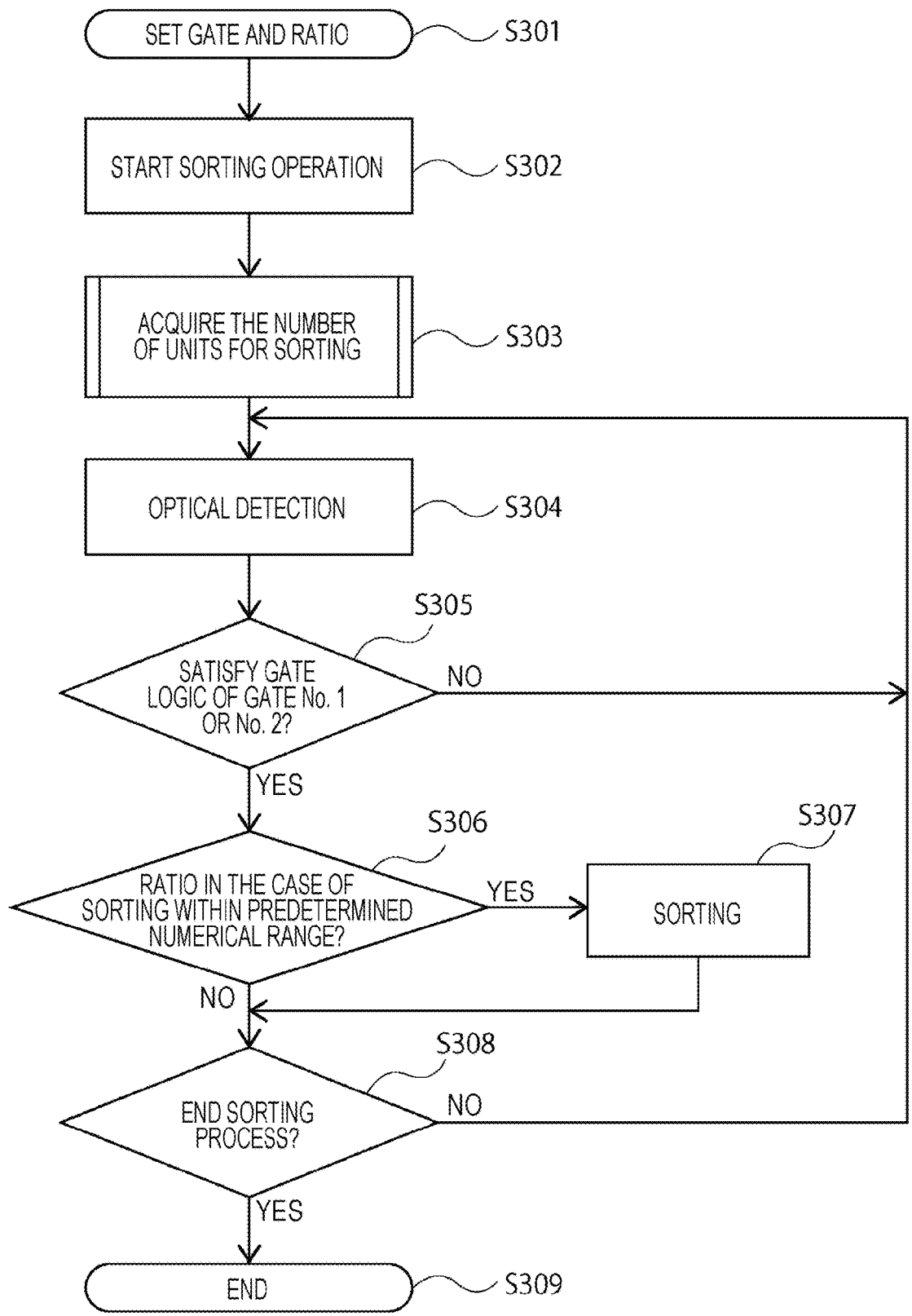

[Fig. 9]
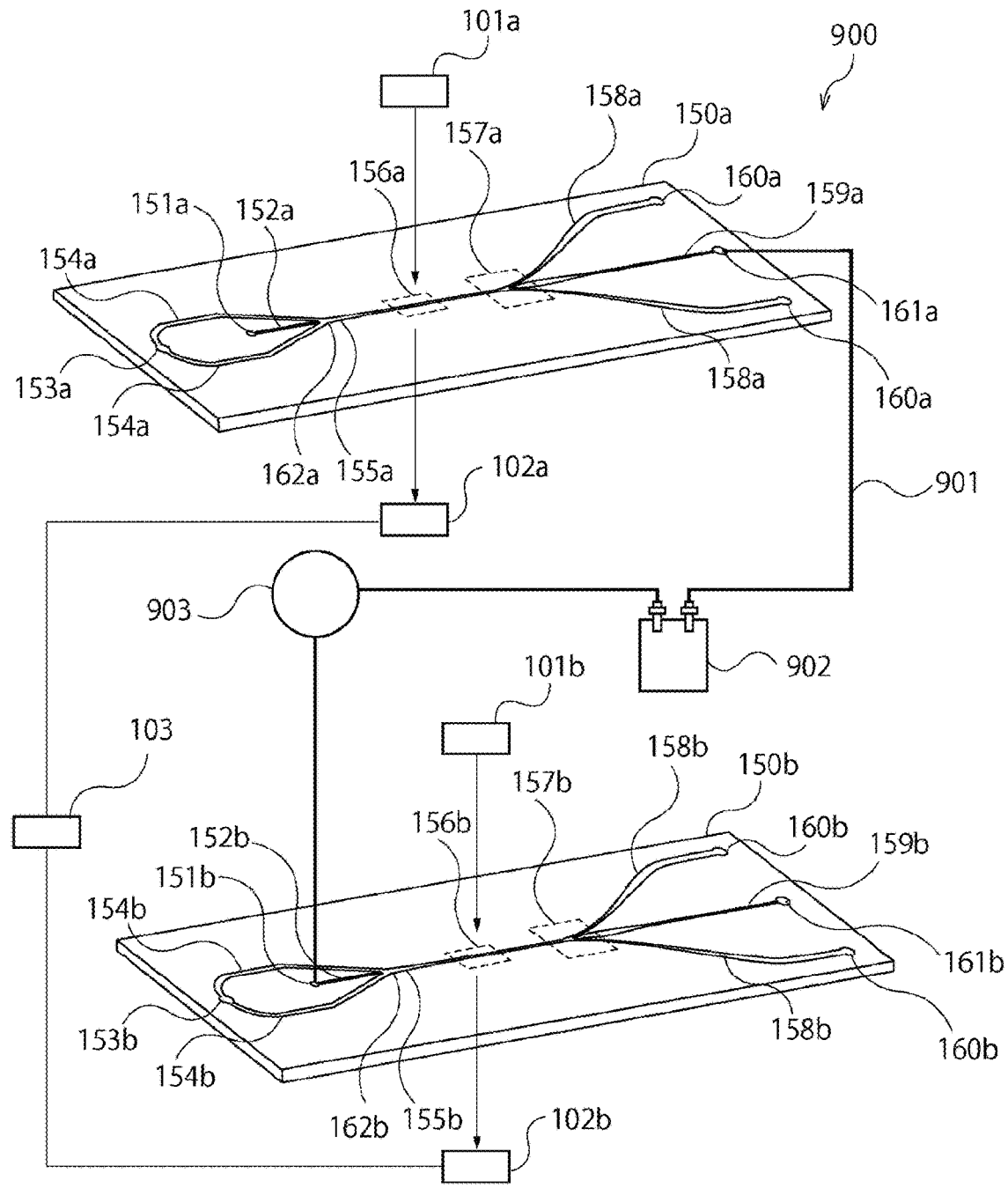

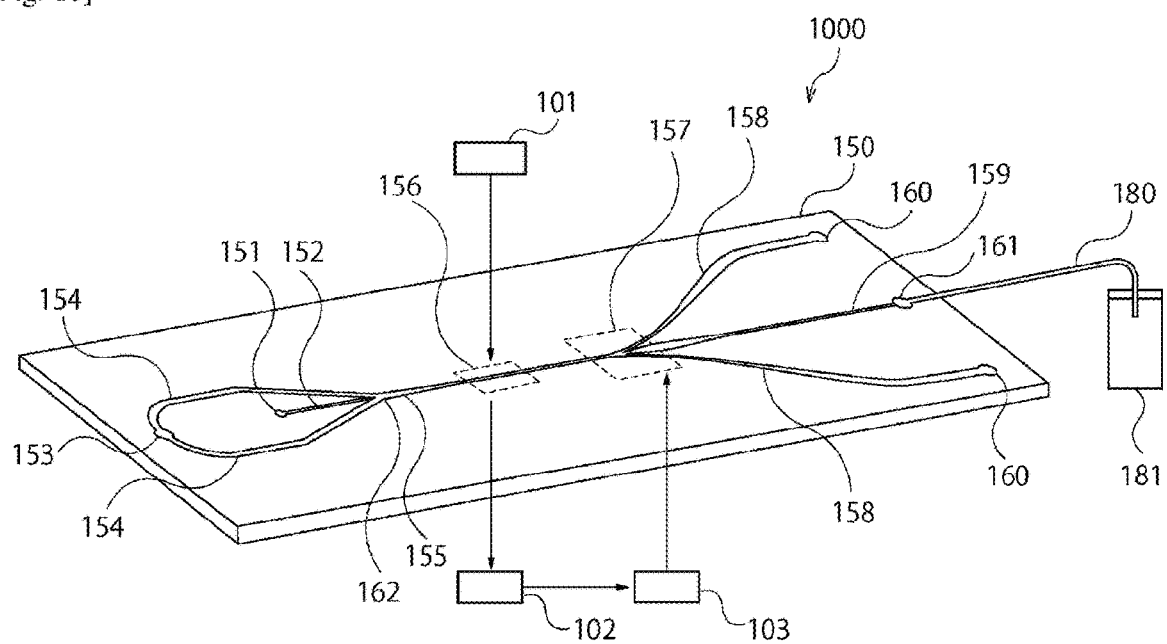
[Fig. 10]

MICROPARTICLE SORTING DEVICE, CELL THERAPEUTIC AGENT MANUFACTURING DEVICE, MICROPARTICLE SORTING METHOD AND PROGRAM

CROSS REFERENCE TO RELATED APPLICATIONS

This application claims the benefit under 35 U.S.C. § 371 as a U.S. National Stage Entry of International Application No. PCT/JP2019/035591, filed in the Japanese Patent Office as a Receiving Office on Sep. 10, 2019, which claims priority to Japanese Patent Application Number JP 2019-161868, filed in the Japanese Patent Office on Sep. 5, 2019, and Japanese Patent Application Number JP 2018-168711, filed on Sep. 10, 2018, each of which is hereby incorporated by reference in its entirety.

TECHNICAL FIELD

The present technology relates to a microparticle sorting device, a cell therapeutic agent manufacturing device, a microparticle sorting method, and a program. More specifically, the present technology relates to a microparticle sorting device, a cell therapeutic agent manufacturing device, a microparticle sorting method, and a program for collecting two or more types of microparticles in a specific constituent ratio.

BACKGROUND ART

Various microparticle sorting devices have been developed so far to sort microparticles. For example, in a particle sorting system for use in a flow cytometer, a laminar flow including a sample liquid including cells and a sheath liquid is discharged from an orifice formed in a flow cell or a microchip. In the discharge, a predetermined vibration is applied to the laminar flow to form droplets. The moving directions of the formed droplets are electrically controlled depending on whether a target particle is included or not, and the target particle is sorted.

Techniques for sorting target particles in a microchip without forming droplets as mentioned above have also been developed. For example, PTL 1 below discloses "a microchip including: a sample liquid introduction channel through which a sample liquid including microparticles flows; at least one pair of sheath fluid introduction channels that merge to the sample liquid introduction channel from both sides thereof, and introduces a sheath liquid around the sample liquid; a merging flow channel in communication with the sample fluid introduction channel and the sheath fluid introduction channel, through which liquids flowing through the introduction channels merge and flow; a negative pressure suction unit in communication with the merging flow channel for sucking and drawing microparticles to be collected; and at least one pair of waste flow channels provided on both sides of the negative pressure suction unit, in communication with the merging flow channel" (claim 1). In the microchip, target particles are collected by suction into the negative pressure suction unit.

CITATION LIST

Patent Literature

PTL 1: JP 2012-127922 A

Non Patent Literature

NPL 1: D Sommermeyer et al., Chimeric antigen receptor-modified T cells derived from defined CD8+ and CD4+ subsets confer superior antitumor reactivity in vivo, Leukemia, 2016 February; 30(2): 492-500

SUMMARY

Technical Problem

The microparticle sorting device obtains multiple types of cell fractions that differ in characteristics, and then mixes the multiple types of cell fractions to obtain a cell mixture including multiple types of cells in a predetermined ratio. The cell mixture can be utilized for treatment, such as, immune cell therapy, for example. For example, NPL 1 mentioned above relates to chimeric antigen receptor T (CAR-T) cells, where the combination of $CD4^+$ CAR-T cells and $CD8^+$ CAR-T cells shows a synergistic antitumor activity (result column).

In order to prepare a cell mixture including multiple types of cells in a predetermined ratio, it is conceivable to, for example, obtain, with a flow cytometer, multiple types of cell subset fractions that have different characteristics, measure/adjust the cell concentration of each cell subset fraction, and then mix the multiple types of cell subset fractions such that the cell content ratio is the predetermined ratio. In this case, however, in addition to the sorting procedure with the flow cytometric, it is necessary to perform a procedure of measuring or adjusting the cell concentration of each cell subset fraction and a procedure of mixing the multiple types of cell subset fractions, which needs much time and effort.

In general, a flow cytometer has a function of performing cell sorting in accordance with the or logic, and the function is used to perform sorting, thereby making it possible to obtain a mixture of multiple types of cells. The cell constituent ratio in the cell mixture obtained by utilizing the function is, however, equal to the cell constituent ratio in a sample subjected to cell sorting. Therefore, the function is not suitable for obtaining a cell mixture that has a desired cell constituent ratio.

In the case of performing a cell sorting operation with the use of the microchip described in PTL 1, typically, only one type of cell that has a certain characteristic is collected into the negative pressure suction unit. Therefore, in order to prepare a cell mixture including multiple types of cells with the use of the microchip, it is necessary to perform a cell sorting operation more than one, which needs much time and labor. Furthermore, in a case where only one type of cell is collected, the other cells flow to the waste flow channel, thus resulting in waste.

The cell sorting in accordance with the or logic with the microchip described in PTL 1 mentioned above is, as with the flow cytometer, not suitable for obtaining a cell mixture that has a desired cell constituent ratio.

There is a need for the present technology to provide a technology for preparing a mixture including multiple types of microparticles in a predetermined ratio.

Solution to Problem

The present inventors have found that the above-mentioned problems can be solved by a microparticle sorting device which has a specific configuration.

In other words, the present technology provides a microparticle sorting device including a determination unit that determines whether microparticles are sorted, on the basis of light generated by irradiating, with light, the microparticles flowing through a flow channel, in which the determination unit performs a primary sorting determination to determine, on the basis of characteristics of the light generated, whether the microparticles belong to any one of two or more different microparticle populations, and then performs a secondary sorting determination to determine whether the microparticles determined to belong to any one of the microparticle populations in the primary sorting determination are sorted, on the basis of the particle constituent ratio specified for the two or more different microparticle populations.

In accordance with one embodiment of the present technology, the microparticle sorting device includes a sorting part that sorts microparticles determined to be sorted in the secondary sorting determination, and the microparticles sorted by the sorting part can be collected in one container.

In accordance with one embodiment of the present technology, the microparticles sorted by the sorting part may be collected in one container, and the constituent ratio of the microparticles in the container can be the specified particle constituent ratio, or fall within a specified numerical range including the specified particle constituent ratio.

As just described, in accordance with one embodiment of the present technology, the microparticle sorting device may include one particle collection channel for collecting the microparticles sorted by the sorting part into one container.

In accordance with one embodiment of the present technology, in the primary sorting determination, the determination unit can determine whether a microparticle belongs to any one of the two or more different microparticle populations, based on whether the light generated by the light irradiation has a feature specified for fluorescence and/or scattered light.

In accordance with one embodiment of the present technology, the determination unit can set the number of acquired particles, on the basis of the specified particle constituent ratio.

In accordance with one embodiment of the present technology, in the secondary sorting determination, the determination unit can determine that the microparticles are sorted if the sorted number of microparticles determined to belong to any one of the two or more different microparticle populations in the primary sorting determination has not reached the number of acquired particles, set on the basis of the specified particle constituent ratio.

In accordance with one embodiment of the present technology, in the secondary sorting determination, the determination unit can determine that the microparticles are not sorted if the sorted number of microparticles determined to belong to any one of the two or more different microparticle populations in the primary sorting determination has reached the number of acquired particles, set on the basis of the specified particle constituent ratio.

In accordance with another embodiment of the present technology, in the secondary sorting determination, the determination unit can determine that the microparticles are sorted if the particle constituent ratio in the case of sorting the microparticles determined to belong to any one of the two or more different microparticle populations in the primary sorting determination falls within a specified numerical range including the specified particle constituent ratio.

In accordance with another embodiment of the present technology, in the secondary sorting determination, the determination unit can determine that the microparticles are not sorted if the particle constituent ratio in the case of sorting the microparticles determined to belong to any one of the two or more different microparticle populations in the primary sorting determination fails to fall within the specified numerical range including the specified particle constituent ratio.

In accordance with one embodiment of the present technology, the microparticle sorting device may include a microchip for microparticle sorting, including a main flow channel through which a fluid including microparticles flows, a branched flow channel branched from the main flow channel, and a particle sorting flow channel that is coaxial with the main flow channel, and the determination unit can determine whether microparticles are sorted, on the basis of light generated by irradiating, with light, the microparticles in the fluid flowing in the microchip for microparticle sorting.

The microparticles can be cells.

The microparticles can be cells, cells determined to be sorted in the secondary sorting determination can be collected in one container, and the cells can be collected in the container are used as a drug.

Furthermore, the present technology also provides a cell therapeutic agent manufacturing device including: a determination unit that determines whether cells are sorted, on the basis of light generated by irradiating, with light, the cells flowing through a flow channel; and a cell sorting part that sorts cells determined to be sorted by the determination unit, in which the determination unit performs a primary sorting determination to determine, on the basis of characteristics of the light generated, whether the cells belong to any one of two or more different cell populations, and then performs a secondary sorting determination to determine whether the cells determined to belong to any one of the cell populations in the primary sorting determination are sorted, on the basis of a cell constituent ratio specified for the two or more different cell populations, and the cells sorted by the cell sorting part are collected in one container.

Furthermore, the present technology also provide a microparticle sorting method including a sorting determination step of determining whether microparticles are sorted, on the basis of light generated by irradiating, with light, the microparticles flowing through a flow channel, in which the sorting determination step includes: a primary sorting determination step of determining, on the basis of characteristics of the light generated, whether the microparticles belong to any one of two or more different microparticle populations; and a secondary sorting determination step of determining, whether the microparticles determined to belong to any one of the microparticle populations in the primary sorting determination step are sorted, on the basis of a particle constituent ratio specified for the two or more different microparticle populations.

Furthermore, the present technology also provides a program for causing a microparticle sorting device or a cell therapeutic agent manufacturing device to execute a sorting determination step of determining whether microparticles are sorted on the basis of light generated by irradiating, with light, the microparticles flowing through a flow channel, the sorting determination step including:

a primary sorting determination step of determining, on the basis of characteristics of the light generated, whether the microparticles belong to any one of two or more different microparticle populations; and a secondary sorting determination step of determining, whether the microparticles determined to belong to any one of the microparticle populations in the primary sorting determination step are sorted, on the basis of a particle constituent ratio specified for the two or more different microparticle populations.

Some embodiments are directed to a microparticle sorting device comprising circuitry configured to: obtain optical information indicating a first microparticle population and a second microparticle population; and control, based on at least one constituent amount for the first microparticle population and the second microparticle population, sorting of a first group of microparticles belonging to the first microparticle population and a second group of microparticles belonging to the second microparticle population to obtain a mixture of microparticles including microparticles both from the first microparticle population and the second microparticle population. In some embodiments, the circuitry is further configured to control sorting of microparticles based on light from the microparticles detected in response to irradiating the microparticles with excitation light as the microparticles flow through a flow channel. In some embodiments, the circuitry is further configured to determine, based on at least one characteristic of the detected light and the optical information, the first group of microparticles as belonging in the first microparticle population and the second group of microparticles as belonging in the second microparticle population. In some embodiments, the at least one characteristic includes a feature of fluorescent light and/or scattered light.

In some embodiments, the microparticle sorting device further comprises a microchip configured to perform the sorting of the first group of microparticles and the second group of microparticles. In some embodiments, the microchip comprises a particle collection channel configured to transport the mixture of microparticles into a container. In some embodiments, the microchip further comprises a main flow channel through which a fluid including microparticles of the first microparticle population and of the second microparticle population flows, and a branched flow channel connected to the main flow channel, wherein the particle collection channel is coaxial with the main flow channel. In some embodiments, the mixture of microparticles is collected in a container.

In some embodiments, the at least one constituent amount includes a range of constituent ratios of the first microparticle population to the second microparticle population, and controlling sorting of the first group of microparticles and the second group of microparticles further comprises obtaining the mixture of microparticles to have a ratio of the first microparticle population to the second microparticle population within the range of constituent ratios.

In some embodiments, controlling sorting of the first group of microparticles and the second group of microparticles further comprises: controlling sorting of a first microparticle in the first group to not include the first microparticle in the mixture of microparticles in response to determining that the mixture of microparticles has a ratio of the first microparticle population to the second microparticle population within the range of constituent ratios; and controlling sorting of a second microparticle in the second group to not include the second microparticle in the mixture of microparticles in response to determining that the mixture of microparticles has a ratio of the first microparticle population to the second microparticle population within the range of constituent ratios.

In some embodiments, controlling sorting of the first group of microparticles and the second group of microparticles further comprises: controlling sorting of a first microparticle in the first group to include the first microparticle in the mixture of microparticles in response to determining that the mixture of microparticles has a ratio of the first microparticle population to the second microparticle population outside the range of constituent ratios; and controlling sorting of a second microparticle in the second group to include the second microparticle in the mixture of microparticles in response to determining that the mixture of microparticles has a ratio of the first microparticle population to the second microparticle population outside the range of constituent ratios.

In some embodiments, the at least one constituent amount is a constituent ratio of the first microparticle population to the second microparticle population.

In some embodiments, the circuitry is further configured to set, based on the at least one constituent amount for the first microparticle population to the second microparticle population, a first number of microparticles to acquire for the first microparticle population and a second number of microparticles to acquire for the second microparticle population.

In some embodiments, controlling sorting of the first group of microparticles and the second group of microparticles further comprises: determining a third number of microparticles of the first microparticle population that has been sorted into the mixture of microparticles; controlling sorting of the first group of microparticles based on comparing the third number of microparticles to the first number of microparticles; determining a fourth number of microparticles of the second microparticle population that has been sorted into the mixture of microparticles; and controlling sorting of the second group of microparticles based on comparing the fourth number of microparticles to the second number of microparticles.

In some embodiments, controlling sorting of the first group of microparticles and the second group of microparticles further comprises: controlling sorting of a first microparticle in the first group to include the first microparticle in the mixture of microparticles in response to determining that the third number of microparticles is less than the first number of microparticles; and controlling sorting of a second microparticle in the second group to include the second microparticle in the mixture of microparticles in response to determining that the fourth number of microparticles is less than the second number of microparticles.

In some embodiments, controlling sorting of the first group of microparticles and the second group of microparticles further comprises: controlling sorting of a first microparticle in the first group to not include the first microparticle in the mixture of microparticles in response to determining that the third number of microparticles equals or is greater than the first number of microparticles; and controlling sorting of a second microparticle in the second group to not include the second microparticle in the mixture of microparticles in response to determining that the fourth number of microparticles equals or is greater than the second number of microparticles.

In some embodiments, the microparticles are cells and the mixture of microparticles is a mixture of cells including cells of a first cell type and cells of a second cell type. In some embodiments, the cells are extracted from human blood.

Some embodiments are directed to a method comprising: obtaining optical information indicating a first microparticle population and a second microparticle population; and controlling, based on at least one constituent amount for the first microparticle population and the second microparticle population, sorting of a first group of microparticles belonging to the first microparticle population and a second group of microparticles belonging to the second microparticle population to obtain a mixture of microparticles including microparticles both from the first microparticle population and the second microparticle population.

In some embodiments, the microparticles are cells and the mixture of microparticles is a mixture of cells including cells of a first cell type and cells of a second cell type. In some embodiments, the method further comprises administering the mixture of cells to a subject as a treatment for a medical condition or disease. In some embodiments, the method further comprises administering the mixture of cells to a subject as an immunotherapy treatment for a medical condition or disease. In some embodiments, the method further comprises extracting the cells from human blood.

Some embodiments are directed to a cell therapeutic agent manufacturing device comprising circuitry configured to: obtain optical information indicating that a first group of cells is a first cell type and a second group of cells is a second cell type; and control, based on at least one constituent amount for the first cell type and the second cell type, sorting of the first group of cells and the second group of cells to obtain a mixture of cells including cells of the first cell type and cells of the second cell type.

In some embodiments, the circuitry is further configured to control sorting of cells based on light from the cells detected in response to irradiating the cells with excitation light as the cells flow through a flow channel.

In some embodiments, the circuitry is further configured to determine, based on at least one characteristic of the detected light and the optical information, the first group of cells as being the first cell type and the second group of cells as being the second cell type.

BRIEF DESCRIPTION OF DRAWINGS

FIG. 1 is a diagram illustrating a configuration example of a microparticle sorting device according to an embodiment of the present technology.

FIG. 2 is an example of the block diagram of a control unit.

FIG. 5 is a diagram showing an example of the gate logic and particle constituent ratio which are specified by the user.

FIG. 6 is an example of a flow diagram for a microparticle sorting process in accordance with an embodiment of the present technology.

FIG. 7 is an example of a flow diagram for a microparticle sorting process in accordance with an embodiment of the present technology.

FIG. 8 is an example of a flow diagram for a microparticle sorting process in accordance with an embodiment of the present technology.

FIG. 9 is a diagram illustrating a configuration example of a microparticle sorting device according to an embodiment of the present technology.

FIG. 10 is a diagram illustrating a configuration example of a cell therapeutic agent manufacturing device according to an embodiment of the present technology.

DESCRIPTION OF EMBODIMENTS

Figure 3A:
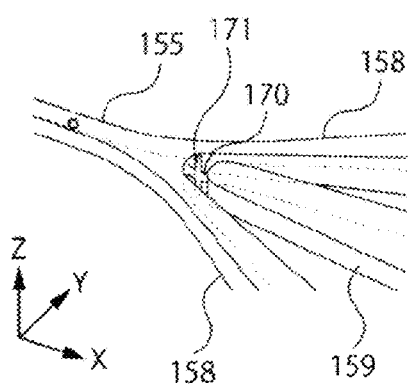
FIGS. 3A to 3C are diagrams illustrating an example of the structure of a sorting part of a microchip for microparticle sorting.

Hereinafter, preferable modes for carrying out the present technology will be described. Note that the embodiments to be described below are intended to provide representative embodiments of the present technology, and the scope of the present technology is not limited to only these embodiments. Note that the present technology will be described in the following order.

1. First Embodiment (Microparticle Sorting Device)
  (1) Description of First Embodiment
  (1-1) Primary Sorting Determination
  (1-2) Secondary Sorting Determination
  (2) First Example of First Embodiment (Example of Microparticle Sorting Operation)
  (3) Second Example of First Embodiment (Example of Microparticle Sorting Operation)
  (4) Third Example of First Embodiment (Example of Microparticle Sorting Operation)
  (5) Fourth Example of First Embodiment (Example of Particle Sorting Process with Connected Microchips for Microparticle Sorting)
2. Second Embodiment (Cell Therapeutic Agent Manufacturing Device)
3. Third Embodiment (Microparticle Sorting Method)

1. FIRST EMBODIMENT (MICROPARTICLE SORTING DEVICE)

(1) Description of First Embodiment

The microparticle sorting device according to the present technology includes a determination unit that determines whether microparticles are sorted, on the basis of light generated by irradiating, with light, the microparticles flowing through a flow channel. The determination unit performs a primary sorting determination to determine, on the basis of characteristics of the light, whether the microparticles belong to any one of two or more different microparticle populations or not, and performs a secondary sorting determination to determine, whether the microparticles determined to belong to any one of the microparticle populations in the primary sorting determination are sorted, on the basis of the particle constituent ratios specified for the two or more different microparticle populations.

A mixture including multiple types of microparticles in a predetermined ratio can be easily obtained by sorting the microparticles in accordance with the determination results in the primary sorting determination and secondary sorting determinations. In particular, the constituent ratio of the multiple types of microparticles in the mixture obtained by the sorting operation can be made the ratio as specified, by performing the secondary sorting determination.

The microparticle sorting device according to the present technology will be described below with reference to FIG. 1 through FIG. 4C.

FIG. 1 is a diagram illustrating a configuration example of a microparticle sorting device according to the present technology. As shown in FIG. 1, the microparticle sorting device 100 according to the present technology includes a light irradiation unit 101, a detection unit 102, a control unit 103, and a microchip 150 for microparticle sorting. As shown in FIG. 2, the control unit 103 includes a signal processing unit 104, a determination unit 105, and a sorting control unit 107.

The light irradiation unit 101 irradiates, with light, microparticles flowing through a flow channel in the microchip 150 for microparticle sorting. The detection unit 102 detects light generated by the light irradiation. Depending on the characteristics of the light detected by the detection unit 102, the control unit 103 controls the flow in the microchip 150 for microparticle sorting, thereby only sorting the microparticles to be collected.

The light irradiation unit 101 irradiates, with light (for example, excitation light or the like), microparticles flowing through a flow channel in the microchip 150 for microparticle sorting. The light irradiation unit 101 can include a light source that emits light, and an objective lens that condenses excitation light on microparticles flowing in the detection area. The light source may be selected appropriately by those skilled in the art, depending on the analysis purpose, and may be, for example, a laser diode, an SHG laser, a solid state laser, a gas laser, or a high-luminance LED, or a combination of two or more thereof. The light irradiation unit may include other optical elements as necessary, in addition to the light source and the objective lens.

The detection unit 102 detects scattered light and/or fluorescence generated from the microparticles by the light irradiation performed by the light irradiation unit 101. The detection unit 102 can include a condenser lens that condenses fluorescence and/or scattered light generated from the microparticles, and a detector. As the detector, a PMT, a photodiode, a CCD, a CMOS, and the like can be used, but the detector is not limited thereto. The detection unit 102 may include other optical elements as necessary, in addition to the condenser lens and the detector. The detection unit 102 can further include, for example, a spectroscopic unit. Optical components constituting the spectroscopic unit can include a grating, a prism, and an optical filter, for example. For example, light with a wavelength to be detected can be separated from light with the other wavelengths, and then detected by the spectroscopic unit. The detection unit 102 can convert the detected light into an analog electrical signal by photoelectric conversion. The detection unit 102 can further convert the analog electrical signal to a digital electrical signal by AD conversion.

The signal processing unit 104 included in the control unit 103 can process the waveform of a digital electrical signal obtained by the detection unit 102, and generate information regarding characteristics of light that is used for the determination made by the determination unit 105 (in particular, primary sorting determination). From the waveform of the digital electrical signal, the signal processing unit 104 can acquire, for example, one, two, or three of the width of the waveform, the height of the waveform, and the area of the waveform as information regarding the characteristics of the light. Furthermore, the information regarding the characteristics of the light may include, for example, the time at which the light is detected.

The determination unit 105 included in the control unit 103 determines whether the microparticles are sorted, on the basis of light generated by irradiating, with light, the microparticles flowing through a flow channel. More specifically, light generated by the light irradiation unit 101 irradiating, with light, the microparticles is detected by the detection unit 102, the waveform of the digital electrical signal obtained by the detection unit 102 is processed by the control unit 103, and then, on the basis of the characteristics of the light generated by the processing, the determination unit 105 determines whether the microparticles are sorted.

Details of the determination made by the determination unit 105 will be described in more detail below in "(1-1) Primary Sorting Determination" and "(1-2) Secondary Sorting Determination".

The sorting control unit 107 included in the control unit 103 controls the microparticle sorting performed by the microchip 150 for microparticle sorting. More particularly, the sorting control unit 107 can control the flow of a fluid in a sorting part 157 in the microchip 150 for microparticle sorting, so as to sort microparticles determined to be sorted by the secondary sorting determination performed by the determination unit 105. In order to control the flow, the sorting control unit 107 can control, for example, driving of an actuator 108 provided in the vicinity of the sorting part. The timing of driving the actuator 108 can be set, on the basis of, for example, the time at which the light is detected.

The control unit 103 may control the light irradiation by the light irradiation unit 101 and/or the light detection by the detection unit 102. Furthermore, the control unit 103 can control driving of a pump for supplying a fluid into the microchip 150 for microparticle sorting. The control unit 103 may include, for example, a hard disk that stores a program for causing the microparticle sorting device to execute the microparticle sorting method according to the present technology and an OS, a CPU, and a memory. The function of the control unit 103 can be achieved in a general-purpose computer, for example. The program may be recorded on a recording medium such as a microSD memory card, an SD memory card, or a flash memory, for example. The drive provided in the microparticle sorting device 100 may read the program recorded on the recording medium, and then, the control unit 103 may cause, in accordance with the read program, the microparticle sorting device 100 to execute the microparticle sorting method according to the present technology.

The microchip 150 for microparticle sorting is provided with a sample liquid inlet 151 and a sheath liquid inlet 153. From these inlets, the sample liquid and the sheath liquid are respectively introduced into the sample liquid channel 152 and the sheath liquid channel 154. The sample liquid includes particles.

The sample liquid and the sheath liquid merge at a merging part 162 to form a laminar flow in which the sample liquid is surrounded by the sheath liquid. The laminar flow flows through a main flow channel 155 toward the sorting part 157.

In the microparticle sorting device 100 according to the present technology, for example, the sorting determination of microparticles can be performed as follows.

The main flow channel 155 is provided with a detection area 156. In the detection area 156, microparticles in the sample liquid flowing through the main flow channel 155 are irradiated with light. The light irradiation is performed by the light irradiation unit 101. The light generated by the light irradiation is detected by the detection unit 102. The detected light can be photoelectrically converted by, for example, the detection unit 102 to generate an analog electrical signal. The analog electrical signal is converted to a digital electrical signal by the signal processing unit 104. On the basis of the digital electrical signal, the determination unit 105 performs a primary sorting determination to determine, on the basis of the characteristics of the light, whether the microparticles belong to any one of two or more different microparticle populations or not. Next, the determination unit 105 performs a secondary sorting determination to determine, whether the microparticles determined to belong to any one of the microparticle populations in the primary sorting determination are sorted, on the basis of the particle constituent ratio specified for the two or more different microparticle populations. The secondary sorting determination can be performed in a case where it is determined in the primary sorting determination that the microparticles belongs to any one of the two or more different microparticle populations.

One position in the detection area 156 may be irradiated with one beam of light, or each of a plurality of positions in the detection area 156 may be irradiated with light. For example, the microchip 150 for microparticle sorting can be configured such that each of two different positions in the detection area 156 is irradiated with light (in other words, in the detection area 156, there are two positions to be irradiated with light). In this case, for example, it can be determined whether the microparticles should be collected or not, on the basis of light (for example, fluorescence and/or scattered light, etc.) generated by irradiating the microparticles with light at one of the positions. Moreover, on the basis of the difference between the detection time of the light generated by the light irradiation at the one position and the detection time of the light generated by light irradiation at the other position, the velocity of the microparticles in the flow channel can be also calculated. For the calculation, the distance between the two irradiation positions may be determined in advance, and the velocity of the microparticles can be determined, on the basis of the difference between the two detection times and the distance. Moreover, on the basis of the velocity, the time of arriving at the sorting part 157 described below can be predicted accurately. The arrival time is accurately predicted, thereby making it possible to optimize the timing of formation of the flow into a particle sorting flow channel 159. Furthermore, in a case where the difference between the arrival time of a certain microparticle at the sorting part 157 and the arrival time of the microparticle before or after the certain microparticle at the sorting part 157 is equal to or less than a predetermined threshold value, it can also be determined that the certain microparticle is not sorted. In a case where the distance is narrow between the certain microparticle and the microparticle before or after the certain microparticle, there is an increased possibility that the microparticle before or after the certain particle may be collected together in suction of the certain microparticle. In a case where there is a high possibility that the microparticles are collected together, determining that the certain microparticle is not sorted can prevent the microparticle before or after the certain microparticle from being collected. Thus, the purity of the target microparticles can be increased among the collected microparticles. Specific examples of a microchip in which each of two different positions in the detection area 156 is irradiated with light and a device including the microchip are described in, for example, JP 2014-202573 A.

In the microparticle sorting device 100 according to the present technology, microparticles determined to be sorted can be collected, for example, as follows.

The microchip 150 for microparticle sorting includes the main flow channel 155 through which a fluid including microparticles flows, branched flow channels that are branched from the main flow channel 155, and the particle sorting flow channel 159 that is coaxial with the main flow channel 155.

In the sorting part 157 in the microchip 150 for microparticle sorting, the laminar flow flowing through the main flow channel 155 is divided to flow into the two branched flow channels 158. Although the sorting part 157 illustrated in FIG. 1 has the two branched flow channels, the number of branched flow channels is not limited to two. The sorting part 157 can be provided with, for example, one or more (for example, two, three, four, etc.) branched flow channels. The branched flow channel may be configured to be branched in a Y-shaped form on one plane as in FIG. 1, or may be configured to be three-dimensionally branched.

Furthermore, in the sorting part 157, only in a case where microparticles flow which have been determined to be sorted by the determination unit 105, a flow into the particle sorting flow channel 159 is formed, and the particles are collected. In this manner, the microparticles determined to be sorted by the determination unit 105 are sorted in the sorting part 157. In other words, the microparticle sorting device 100 according to the present technology may include the sorting part 157 that sorts microparticles determined to be sorted by the determination unit 105.

The formation of the flow into the particle sorting flow channel 159 can be performed, for example, by generating a negative pressure in the particle sorting flow channel 159. In order to generate the negative pressure, an actuator can be attached to the outside of the microchip 150, for example, such that the wall of the particle sorting flow channel 159 can be deformed. The deformation of the wall can change the inside space of the particle sorting flow channel 159 to generate the negative pressure. The actuator can be, for example, a piezo actuator. In a case where it is determined by the determination unit 105 that microparticles should be collected, the sorting control unit 107 can drive the actuator to generate a negative pressure in the particle sorting flow channel 159.

As stated above, in a case where the difference between the arrival time of a certain microparticle at the sorting part 157 and the arrival time of the microparticle before or after the certain microparticle at the sorting part 157 is equal to or less than a predetermined threshold value, the determination unit 105 may also determine that the certain microparticle is not sorted.

In addition, as stated above, in a case where microparticles are introduced into the particle sorting flow channel 159 by generating a negative pressure in the particle sorting flow channel 159, the number of times in which the negative pressure can be continuously generated may be limited depending on, for example, the acceptable limit of the deformation particle sorting flow channel 159. For that reason, in a case where an actuator is continuously driven at the predetermined number of times, for example, the determination unit 105 may determine that a microparticle flowing next is not sorted.

The particles, determined not to be sorted as described above, flow into either of the two branched flow channels 158.

Figure 3B:
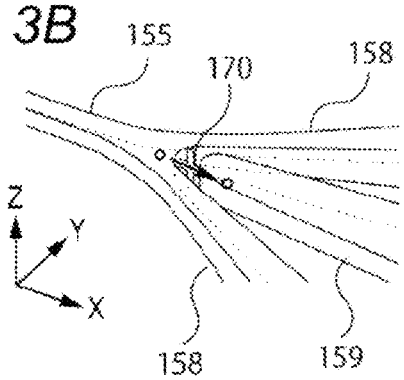
Figure 3C:
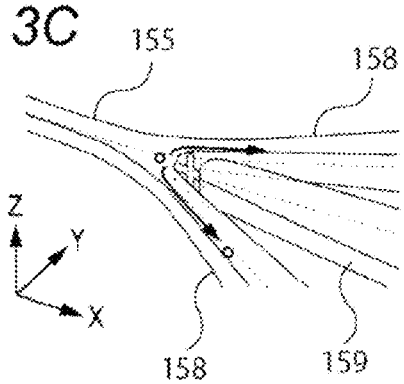

An enlarged view of the sorting part 157 is shown in FIGS. 3A to 3C. As shown in FIG. 3A, the main flow channel 155 and the particle sorting flow channel 159 are communicated with each other via an orifice part 170 that is coaxial with the main flow channel 155. Particles that should be collected flow through the orifice part 170 into the particle sorting flow channel 159 as shown in FIG. 3B. Particles that should not be collected flow into the branched flow channels 158 as shown in FIG. 3C.

In order to prevent particles that should not be collected from entering the particle sorting flow channel 159 through the orifice part 170, the orifice part 170 may be provided with a gate flow inlet 171. The sheath liquid is introduced from the gate flow inlet 171, and the introduced sheath liquid partially forms a flow from the orifice part 170 toward the main flow channel 155, thereby preventing particles that should not be collected from entering the particle sorting flow channel 159. Note that the rest of the introduced sheath fluid flows into the particle sorting flow channel 159.

The laminar flow flowing to the branched flow channels 158 can be discharged to the outside of the microchip at branched channel ends 160. Furthermore, the particles collected into the particle sorting flow channel 159 can be discharged to the outside of the microchip at a particle sorting channel end 161.

In this manner, in the microchip 150, the microparticles are sorted into the particle sorting flow channel 159.

Note that in the present technology, the term "micro" means that the flow channel included in the microchip at least partially has a dimension on the order of μm, in particular, has a cross-sectional dimension on the order of μm. In other words, in the present technology, the term "microchip" refers to a chip including a flow channel on the order of μm, in particular, a chip including a flow channel that has a cross-sectional dimension on the order of μm. For example, a chip including a particle sorting part provided with flow channels that has a cross-sectional dimension on the order of μm can be referred to as a microchip according to the present technology. According to the present technology, the cross section of the main flow channel 155 is, for example, rectangular, and the width of the main flow channel 155 can be, for example, 100 μm to 500 μm, particularly 100 μm to 300 μm in the sorting part 157. The width of the branched flow channel 158 may be smaller than the width of the main flow channel 155. The cross section of the orifice part 170 is, for example, circular, and the diameter of the orifice part 170 at the connection between the orifice part 170 and the main flow channel 155 can be, for example, 10 μm to 60 μm, in particular, 20 μm to 50 μm. These dimensions for the flow channels may be changed appropriately, depending on the sizes of the microparticles.

One container can be connected to the particle sorting channel end 161. The microparticles sorted by the sorting part 157 are collected in the container. In other words, the microparticle sorting device 100 according to the present technology includes the sorting part 157 that sorts microparticles determined to be sorted by the determination unit 105, the microparticles sorted by the sorting part 157 can be collected in one container. Then, the constituent ratio of the microparticles in the container can be the specified particle constituent ratio, or fall within a specified numerical range including the specified particle constituent ratio.

One particle collection channel may be connected to the particle sorting channel end 161. One end of the particle collection channel may be connected to the particle sorting channel end 161, and the other end thereof can be connected to one container (not shown) for collecting microparticles sorted in the particle sorting flow channel 159. As just described, in accordance with one embodiment of the present technology, the microparticle sorting device 100 may include one particle collection channel for collecting the microparticles sorted by the sorting part 157 into one container. The sorted microparticles are collected in the container through the particle collection channel.

According to the present technology, the microparticles may be appropriately selected by those skilled in the art. According to the present technology, the microparticles can encompass biological microparticles such as cells, microorganisms, and liposomes; synthetic microparticles such as latex particles, gel particles, and industrial particles; and the like. The biological microparticles can include chromosomes, liposomes, mitochondria, organelles (cellular organelles) and the like that constitute various cells. The cells can include animal cells (such as blood cells) and plant cells. The microorganisms can include bacteria such as *E. coli*, viruses such as tobacco mosaic virus, fungi such as yeast, and the like. Moreover, the biological microparticles can also encompass biological macromolecules such as nucleic acids, proteins, and complexes thereof. Furthermore, the synthetic microparticles may be microparticles including, for example, organic or inorganic polymer materials, metals, or the like. The organic polymer materials can include polystyrene, styrene-divinyl benzene, and polymethyl methacrylate. The inorganic polymer materials can include glass, silica, magnetic materials, and the like. The metals can include gold colloids, aluminum, and the like. The shapes of the microparticles may be spherical or substantially spherical, or non-spherical. The size and mass of the microparticles can be selected appropriately by those skilled in the art, depending on the size of the flow channel of the microchip. On the other hand, the size of the flow channel of the microchip can also be selected appropriately, depending on the size and mass of the microparticles. According to the present technology, a chemical or biological label, for example, a fluorescent dye or the like, can be attached to the microparticles, if necessary. The label can make the detection of the microparticles easier. The label to be attached can be selected appropriately by those skilled in the art.

According to one embodiment of the present technology, the microparticles are cells, and the cells collected in the container can be used as a drug. In the container, multiple types of cells are collected in specified cell constituent ratios. For example, in order to produce a cell therapeutic agent, multiple types of cells may be necessary to be contained in one container at a specified constituent ratio. Therefore, this embodiment is suitable, for example, for producing cell therapeutic agents.

The fluid flowing through the microchip 150 for microparticle sorting is, for example, a liquid, a matter in liquid form, or a gas, preferably a liquid. The type of the fluid may be selected appropriately by those skilled in the art, depending on, for example, the type of microparticles to be sorted, or the like. For example, commercially available sheath fluids and sample fluids, or sheath fluids and sample fluids known in the art may be used as the fluid.

The microchip 150 for microparticle sorting can be manufactured by methods known in the art. For example, the microchip 150 for microparticle sorting can be manufactured, for example, by bonding two substrates which have a predetermined flow channel formed. The flow channel may be formed in both of the two substrates, or may be formed in only one of the substrates. In order to make it easier to adjust the position in bonding the substrates, the flow channel may be preferably formed only in one of the substrates.

Materials known in the art can be used as materials for forming the microchip 150 for microparticle sorting. For example, the materials include, but are not limited to, polycarbonate, cycloolefin polymers, polypropylene, polydimethyl siloxane (PDMS), polymethyl methacrylate (PMMA), polyethylene, polystyrene, glass, and silicon. For example, polymer materials such as polycarbonate, cycloolefin polymers, and polypropylene are particularly preferred, in particular, because the materials are excellent in workability, and can be adapted to inexpensively manufacture microchips with the use of a molding device.

The primary sorting determination and the secondary sorting determination performed by the determination unit constituting the microparticle sorting device according to the present technology will be described in more detail below.

(1-1) Primary Sorting Determination

The determination unit 105 determines which one of the two or more different microparticle populations a microparticle belongs to, on the basis of the characteristics of the light generated by the light irradiation by the light irradiation unit 101. The foregoing determination is the primary sorting determination according to the present technology. It can be determined in the primary sorting determination whether the microparticle belongs to any one of, for example, 2 to 20, in particular 2 to 10, more particularly 2 to 5 different microparticle populations.

Each of the two or more different microparticle populations can include one or more microparticles (in particular, a plurality of microparticles) that share a feature. In other words, each of one or more microparticles constituting each microparticle population has the feature (hereinafter, also referred to as a "microparticle feature").

The term "different" in the present technology can mean that the microparticle feature differs between or among the two or more microparticle populations. In other words, it may be the meaning of the term "different" in the present technology that the feature shared by the plurality of microparticles constituting each microparticle population differs between or among two or more microparticle populations.

For example, in a case where the microparticles are cells, a plurality of cells constituting each of the two or more different microparticle populations (cell populations) can share a feature. The feature may be, for example, a feature on the surface of a cell, a feature on the inside of a cell, a feature on the shape of a cell, a feature on the size of a cell, or a combination of these features. Examples of the feature on the surface of the cell can include, for example, a compound (in particular, surface antigen) present on the cell surface. Examples of the feature on the inside of the cell can include the complexity of the internal structure and/or a compound present inside the cell.

According to one embodiment of the present technology, in a case where the microparticle is a cell, the feature may be the size of the cell, the complexity of the internal structure, a compound present inside the cell, or a compound present on the cell surface, or a combination thereof. Depending on the size of the cell, the complexity of the internal structure, the compound present inside the cell, or the compound present on the cell surface, or a combination thereof, for example, the type of the cell, in particular blood cell, can be identified. Those skilled in the art can appropriately select the cell feature necessary to identify the cell type.

An example of blood cell classification will be described below. Blood cells are classified by CD classification. For example, CD45 is an antigen common to leukocytes, and for example, leukocytes can be selected from blood cells in response to CD45 and side scattered light (SSC), and moreover, lymphocytes can also be selected exclusively among the leukocytes. Furthermore, CD3 is one of pan-T cell antigens, that is, the fact that a lymphocyte is CD3+ (positive) means that the lymphocyte is a T cell. Furthermore, the fact that the T cell is CD4+ means that the T cell is a helper T cell, and the fact that the T cell is CD8+ means that the T cell is a cytotoxic T cell. T cells are typically positive for any one of CD4 and CD8.

As described above, helper T cells and cytotoxic T cells can be selected from blood cells by gating with CD45 and SSC, gating with CD3, and gating with CD4 or CD8.

As stated above, in a case where the microparticles are cells, the two or more different microparticle populations (in this case, the microparticle population refers also to a cell population) may be classified by a molecule (such as an antigen) present on the cell surface.

Also, the two or more cell populations may be classified by a differentiation stage; that is, may be two or more cell populations in a different differentiation stage. It is known, for example, that T-cells have differentiation stages of a naive T-cell, a stem cell-like memory T-cell ($T_{scm}$), a central memory T-cell ($T_{CM}$), an effector memory T-cell ($T_{EM}$), a resident memory T-cell ($T_{RM}$), and an effector T-cell ($T_{EFF}$). The two or more cell populations may be, for example, two cell populations of a combination of a cell population being in one differentiation stage among the multiple differentiation stages as described above, and a cell population being in another differentiation stage, or three or more cell populations of a combination of the two cell populations and one or more cell populations being in one or more other differentiation stages.

Furthermore, the two or more cell populations may be classified by a combination of a surface antigen and a differentiation stage; that is, may be two or cell populations having different surface antigens and/or being in different differentiation stages. For example, the T-cells are classified by the surface antigen, CD4+ or CD8+, as described above. Further, the T-cells are classified by the differentiation stage, as described above. Then, the T-cells may be classified into the two or more cell populations by the combination of the surface antigen and the differentiation stage.

For example, the T-cells may be classified into the following two cell populations:
   cells being CD8+ in the differentiation stage of the central memory T-cell, and
   cells being CD4+ in the differentiation stage of the naive T-cell.

For example, the T-cells may be classified into the following four cell populations:
   cells being CD8+ in the differentiation stage of the naive T-cell,
   cells being CD8+ in the differentiation stage of the central memory T-cell,
   cells being CD4+ in the differentiation stage of the naive T-cell, and
   cells being CD4+ in the differentiation stage of the central memory T-cell.

Note that the surface antigen and the differentiation stage specified are not limited to these examples, and may be other antigens and other differentiation stages.

The microparticle feature can be reflected in the characteristics of light generated by irradiating the microparticle with light. Therefore, according to the present technology, the primary sorting determination is performed, on the basis of the characteristics of the light generated by the light irradiation. In other words, the characteristics of the light determine whether a certain microparticle has a feature (microparticle feature) that indicates that the microparticle belongs to any one of the two or more different microparticle populations. The light may be, for example, scattered light and/or fluorescence. The scattered light may be, for example, forward scattered light and/or side scattered light and/or back scattered light. The characteristics of the light may be, for example, the wavelength and/or intensity of the light, in particular the wavelength and/or intensity of the scattered light or fluorescence.

According to the present technology, in order to determine whether a microparticle belongs to any one of the two or more different microparticle populations, it can be determined whether the characteristics of the light generated by the light irradiation satisfy criteria specified for light (hereinafter, referred to as a "primary sorting criteria"). Since the primary sorting criteria are set for each of the two or more different microparticle populations, two or more primary sorting criteria may be used in the primary sorting determination. The number of primary sorting criteria may be selected depending on the number of microparticle populations determined on whether any microparticle belongs to the populations in the primary sorting determination, and in particular, can be the same number as the number of microparticle populations. In other words, the number of primary sorting criteria may be selected depending on the number of types of microparticles (in particular, cells) to be sorted, and for example, can be the same number as the number of types of microparticles (in particular, cells) to be sorted. For example, in the primary sorting determination, primary sorting criteria of 2 to 20 may be used, particularly, primary sorting criteria of 2 to 10 may be used, and more particularly, primary sorting criteria of 2 to 5 may be used. For example, in the case of sorting two cell populations from a liquid including many types of cells with the microparticle sorting device according to the present technology, two primary sorting criteria respectively corresponding to the two cell populations are used.

The primary sorting criteria can be specified in advance, prior to performing the microparticle sorting process in accordance with the present technology. For example, a user who uses the microparticle sorting device according to the present technology can specify the primary sorting criteria in advance. The primary sorting criteria can be specified, for example, by a user who sets gating for a histogram, a density plot, or a spectrum obtained by making a test measurement for a microparticle-containing sample with the microparticle sorting device according to the present technology. The test measurement can include, for example, the acquisition of a light-related feature of each microparticle in the sample by the microparticle sorting device 100 (in particular, the light irradiation unit 101, the detection unit 102, and the signal processing unit 104), without performing the sorting determination by the determination unit 105 and the sorting control unit 107. On the basis of the acquired light-related feature of each microparticle, microparticle sorting device 100 can generate a histogram, a density plot, or a spectrum.

In accordance with one embodiment of the present technology, in the primary sorting determination, the determination unit 105 can determine whether a microparticle belongs to any one of the two or more different microparticle populations, based on whether the light generated by the light irradiation has a feature specified for fluorescence and/or scattered light. In this embodiment, primary sorting criteria respectively corresponding to the two or more different microparticle populations can be specified, for example, by a user prior to the primary sorting determination. It can be determined that a microparticle belongs to any of the two or more different microparticle populations in a case where the characteristics of the fluorescence and/or scattered light generated by the light irradiation satisfy any one of the two or more primary sorting criteria specified, and it can be determined that a microparticle belongs to none of the two or more different microparticle populations in a case where the characteristics satisfy none of the two or more primary sorting criteria specified.

The primary sorting criteria may be criteria regarding the wavelength and/or intensity of light, and for example, examples of the primary sorting criteria can include, for example, the following:
whether the light has a wavelength within a specified wavelength range;
whether the light has an intensity within a specified intensity range; or
whether the ratio between the light intensity of light with a certain wavelength and the intensity of light with other wavelengths falls within the specified range.

The primary sorting criteria may be one of the foregoing criteria, or two or more thereof.

Furthermore, the primary sorting criteria may include a criterion for the determination of microparticles, based on the time when the light is detected. For example, a threshold value is set for the time interval of the microparticles detected closely. More specifically, the criteria for the determination can be whether within a predetermined period of time before and after the time when a certain microparticle is detected, another microparticle is detected or not. The set threshold value corresponds to the predetermined period of time. The adoption of the criteria for the determination can prevent a microparticle that should not be sorted from being collected, for example, in a case where two adjacent microparticles are detected and one of the two microparticles should not be sorted. Thus, the purity of the microparticles to be sorted can be increased.

The criteria for the determination of the microparticles, based on the time, may be adopted or unadopted as the primary sorting criteria by, for example, setting in advance whether the user performs sorting with priority on purity or sorting with priority on yield.

In the case of setting for sorting performed with priority on purity, the criteria for the determination of microparticle, based on the time, may be adopted as the primary sorting criteria. In this case, when a certain microparticle is detected which satisfies the criterion for the determination of wavelength range and/or light intensity, it is determined whether or not there is further another microparticle (for example, a microparticle or the like determined not to be sorted) within the threshold value of the time interval before and after the time when the certain microparticle is detected. If there is another microparticle, it is determined that the certain microparticle is not sorted. If there is not another microparticle, it is determined that the certain microparticle is sorted.

In the case of setting for sorting performed with priority on yield, the criteria for the determination of microparticle, based on the time, may be unadopted as the primary sorting criteria. In other words, it is determined that sorting is performed, regardless of the determination of a microparticle before and after the time when a microparticle is detected which satisfies the criterion for the determination of wavelength range and/or light intensity.

The threshold value of the time interval may be set to be another threshold value for each of before and after the time when the microparticle is detected.

As stated above, the determination unit 105 may determine whether or not there is another microparticle within the threshold value of the time interval before and after the time when the certain microparticle is detected, and may determine that the certain microparticle is not sorted if there is another microparticle; that is, the determination unit 105 may determine that the certain microparticle is not sorted, in accordance with the presence of the other microparticle present in the vicinity of the certain microparticle.

In addition, as explained above, the determination unit 105 may determine that the microparticle flowing next is not sorted in accordance with the drive of the actuator continuously driven at the predetermined number of times.

The determination unit 105 may count the number of times in which the determination unit 105 determines that the microparticle flowing next is not sorted in accordance with the presence of the other microparticle in the vicinity of the certain microparticle, the number of times in which the certain microparticle is not sorted and/or the drive of the actuator continuously driven at the predetermined times. The number of times counted as above in which the microparticle is determined to be not sorted is used, for example, for obtaining the number of microparticles sorted, as explained in "(1-2) Secondary Sorting Determination" described below.

The primary sorting determination may be, for example, cell sorting determination by light irradiation and light detection performed in on-chip sorting with the use of the microchip described in PTL 1 mentioned above or the like. For example, in the microchip described in PTL 1 mentioned above, light generated by irradiating, with light, cells flowing through a flow channel is detected, and then, on the basis of the characteristics of the detected light, it is determined whether the cells are sorted. Such sorting determination may be performed as the primary sorting determination.

(1-2) Secondary Sorting Determination

The determination unit 105 determines whether the microparticles determined to belong to any one of the two or more different microparticle populations in the primary sorting determination are sorted, on the basis of the particle constituent ratio specified for the two or more different microparticle populations. The foregoing determination is the secondary sorting determination according to the present technology.

The secondary sorting determination may be performed, for example, after the sorting determination based on the characteristics of light in on-chip sorting with the use of the microchip described in PTL 1 mentioned above or the like. In a case where the present technology is applied to the on-chip sorting, the secondary sorting determination is performed after the sorting determination based on the characteristics of light, and thereafter, the operation of sorting the microparticles is performed.

As just described, according to the present technology, the secondary sorting determination is further performed between the primary sorting determination and the microparticle sorting operation, thereby making it possible to obtain, in a simple way, a mixture including multiple types of microparticles in predetermined constituent ratios.

The secondary sorting determination process can be implemented in various microparticle sorting devices, and can be incorporated into, in particular, a microparticle sorting device that performs a sorting determination made by irradiating microparticles with light and a microparticle sorting operation based on the determination result. For example, in a microparticle sorting device that performs on-chip sorting with the use of the microchip described in PTL 1 mentioned above or the like, the secondary sorting determination can be performed.

The particle constituent ratios are specified in advance, prior to performing the microparticle sorting process in accordance with the present technology. For example, a user who uses the microparticle sorting device according to the present technology can specify the particle constituent ratios in advance. For example, the particle constituent ratios may be the constituent ratios of two or more different microparticle populations, for example, the constituent ratios of 2 to 20 different microparticle populations, particularly the constituent ratios of 2 to 10 different microparticle populations, more particularly the constituent ratios of 2 to 5 different microparticle populations. The number of microparticle populations for which the particle constituent ratio is specified can correspond to the number of microparticle populations in the primary sorting determination.

For example, in the case of sorting two different microparticle populations A and B in accordance with the present technology, for example, the user can specify the particle constituent ratio (the number of microparticles that belong to the microparticle population A: the number of microparticles that belong to the microparticle population B), for example, within the numerical range of more than 0:less than 100 to less than 100:more than 0, particularly 0.1:99.9 to 99.9:0.1, more particularly 1:99 to 99:1. Also in the case of sorting three or more microparticle populations in accordance with the present technology, the user can similarly specify the particle constituent ratios.

For example, in a case where the two or more microparticle populations are classified by the molecule present on the cell surface and/or the differentiation stage, as stated in "(1-1) Primary Sorting Determination" described above, a particle constituent ratio of each microparticle population may be specified by a user. For example, as for four cell populations of cells of CD8+ in the differentiation stage of the naive T-cell, cells of CD8+ in the differentiation stage of the central memory T-cell, cells of CD4+ in the differentiation stage of the naive T-cell, and cells of CD4+ in the differentiation stage of the central memory T-cell, the same particle constituent ratio (25:25:25:25) may be specified, or a different particle constituent ratios (for example, 20:40:30:10, or the like) may be specified.

Before performing the secondary sorting determination, the determination unit 105 can set, on the basis of the specified particle constituent ratio, criteria (hereinafter, also referred to as "secondary sorting criteria") for determining whether the microparticles determined to belong to any one of the two or more different microparticle populations in the primary sorting determination are sorted. The secondary sorting criteria can be set such that the particle constituent ratio is achieved by sorting the microparticles determined to belong to any one of the two or more different microparticle populations in the primary sorting determination. The secondary sorting criteria may be set by, for example, the determination unit 105, or may be set by another component.

In accordance with one embodiment of the present technology, the determination unit 105 may set the number of acquired particles, on the basis of the specified particle constituent ratios. According to the present technology, "the number of acquired particles" means the number of microparticles to be sorted. According to this embodiment, for example, it can be used as a secondary sorting criterion whether microparticles to be sorted have already been acquired or not to reach the number of the acquired particles. The number of acquired particles can be set for each of the two or more different microparticle populations. The number of acquired particles may be specified by the determination unit 105, on the basis of the result of the test measurement.

For example, in response to the fact that the user specifies, as the particle constituent ratio between two different microparticle populations A and B, 50:50 (i.e., the number of microparticles that belong to the microparticle population A: the number of microparticles that belong to the microparticle population B=50:50), the determination unit 105 can set, for example, the numbers of acquired particles for the microparticles that belong to the microparticle populations A and B to, for example, 100 and 100, or 200 and 200, respectively.

The determination unit 105 can determine that microparticles are sorted as long as the set number of acquired particles is not exceeded. More specifically, the determination unit 105 can determine that the microparticles are sorted if the sorted number of microparticles determined to belong to any one of the two or more different microparticle populations in the primary sorting determination has not reached the number of acquired particles, set on the basis of the specified particle constituent ratio. The determination unit 105 can determine that the microparticles are not sorted if the sorted number of microparticles determined to belong to any one of the two or more different microparticle populations in the primary sorting determination has reached the number of acquired particles, set on the basis of the specified particle constituent ratio. According to the present technology, "the sorted number" means the number of microparticles already sorted.

For example, a case is assumed where the numbers of acquired particles for the two different microparticle populations A and B are respectively set to 100 and 100, and the sorted number of the microparticle population A is 100, and the sorted number of the microparticle population B is 99. In this case, if it is determined that a microparticle belongs to the microparticle population A in the primary sorting determination, the determination unit 105 determines that the microparticle is not sorted, because the sorted number of the microparticle population A to which the microparticle belongs is 100, that is, the number of acquired particles has been reached. On the other hand, if it is determined that a microparticle belongs to the microparticle population B in the primary sorting determination, the determination unit 105 determines that the microparticle is sorted, because the sorted number of the microparticle population B to which the microparticle belongs is 99, that is, the number of acquired particles has not been reached.

When the determination unit 105 performs the secondary sorting determination as just described, the collected microparticles have the particle constituent ratio mentioned above.

The sorted number of the microparticles can be acquired by counting the number of microparticles passing through a predetermined position in the particle sorting flow channel 159. In other words, the frequency at which microparticles pass through a predetermined position in the particle sorting flow channel 159 may be used as the sorted number of the microparticles. For the purpose of the counting, for example, light irradiation can be performed toward the predetermined position in the particle sorting flow channel 159. When the microparticles pass through the predetermined position, light is generated from the microparticles by the light irradiation. The passage of the microparticles can be detected by detecting the light. The frequency at which the light is detected may be used as the passing frequency. In order to detect the passage of the microparticles as described above, for example, a light irradiation unit that emits light toward the predetermined position and a detection unit that detects the light generated by the light irradiation can be provided in the microparticle sorting device 100. The contents described above with respect to the light irradiation unit 101 and the detection unit 102 apply to the light irradiation unit and the detection unit. The counting may be performed by, for example, the control unit 103.

Alternatively, the sorted number of the microparticles can be acquired, for example, by counting the number of sorting operations performed by the sorting control unit 107. In other words, the number of sorting operations performed by the sorting control unit 107 may be used as the sorted number of the microparticles. The counting may be performed by the control unit 103, and in particular, can be performed by the sorting control unit 107.

Alternatively, the sorted number of the microparticles can be acquired, for example, by counting the number of determinations made by the determination unit 105 to determine that sorting is to be performed. In other words, the number of determinations made by the determination unit 105 to determine that sorting is to be performed may be used as the sorted number of the microparticles. The counting may be performed by the control unit 103, and in particular, can be performed by the determination unit 105.

Alternatively, the number of the microparticles sorted may be obtained by subtracting the number of determinations in which it belongs to the certain microparticle population but is not sorted from the number of the determinations in which it belongs to the certain microparticle population. The sorted number can be exactly counted by obtaining the sorted number as described above.

The number of determination in which it belongs to the certain microparticle population may be the number of determination in which the determination unit 105 determines that it belongs to the certain microparticle population, as stated in "(1-1) Primary Sorting Determination" described above.

In addition, the number of determination in which it belongs to the certain microparticle population but is not sorted may be the number of determination by the determination unit 105 not to be sorted, as stated in "(1-1) Primary Sorting Determination". Accordingly, it may be the total of (the number of determinations in which the determination unit 105 determines that the certain microparticle is not sorted according to the presence of another microparticle in the vicinity of the certain microparticle) and (the number of determinations in which the determination unit 105 determines that the microparticle flowing next is not sorted according to the drive of an actuator continuously driven at the predetermined number of times), or may be either of the two numbers.

According to another embodiment of the present technology, the determination unit 105 can determine that the microparticles are sorted, as long as the constituent ratio of the collected microparticles falls within a predetermined numerical range including the specified particle constituent ratio. In other words, whether the constituent ratio of the collected microparticles falls within a predetermined numerical range including the specified particle constituent ratio can be used as a secondary sorting criterion.

More specifically, the determination unit 105 can determine that the microparticles are sorted if the particle constituent ratio in the case of sorting the microparticles determined to belong to any one of the two or more different microparticle populations in the primary sorting determination falls within the specified numerical range including the specified particle constituent ratio. The determination unit 105 can determine that the microparticles are not sorted if the particle constituent ratio in the case of sorting microparticles determined to belong to any one of the two or more different microparticle populations in the primary sorting determination fails to fall within the specified numerical range including the specified particle constituent ratio.

The determination unit 105 can adopt, for example, a specified particle constituent ratio ± a predetermined threshold value as the specified numerical range. More specifically, for example, in a case where a user specifies 50:50 as the particle constituent ratio between the two different microparticle populations A and B, the particle constituent ratio (50) ± a predetermined threshold value (for example, 0.05) specified for each population, i.e., 49.5 to 50.5 can be adopted as the specified numerical range. The threshold value may be set by the user of the microparticle sorting device in accordance with the present technology.

The determination unit 105 performs the secondary sorting determination as just described, thereby allowing more microparticles to be collected in constituent ratios within the specified numerical range.

As explained in (1-1) and (1-2), the microparticle sorting device according to the present technique determines whether the microparticles belong to any one of two or more different microparticle populations, and then whether the microparticle determined to belong to any one of the two or more different microparticle population are sorted on the basis of the specified particle constituent ratio. The microparticles determined to be sorted flow into a particle sorting flow channel 159 through the orifice part 170. One container may be connected to the particle sorting channel end 161 through, for example, a particle collection channel. The microparticles determined to be sorted, accordingly, go out from the particle sorting channel end 161, and flow into the one container through the particle collection channel. As described above, in the microparticle sorting device according to the present technique, the two or more different microparticle populations flow into the one container through one particle sorting flow channel 159.

Here, when the microparticle population refers to the "class" and the flow from the orifice part 170 to the container refers to the "stream", it may be considered that two or more different classes are assigned by the microparticle sorting device of the present technology, and when a relationship in which the number of the classes are more than the number of the streams is established, a mixture including two or more classes in predetermined ratios may be obtained.

For example, a case where four types of classes are specified is supposed. In this case, the four types of the classes are assigned to one stream by the microparticle sorting device of the present technology, whereby four types of classes can be sorted at the same time. In addition four classes are classified into two by the microparticle sorting device of the present technology (for example, classes A-D are classified into classes A and B and classes C and D), and the two classes, classified into two, may be assigned to two streams (for example, the classes A and B are assigned to stream 1, and the classes C and D are assigned to stream 2). Embodiments of assigning to two or more streams may be adopted, for example, in a flow cytometer described below. In this case, one stream may contain from a part at which a running direction of liquid droplets to which an electric charge is applied is changed to a container for recovering the liquid droplets. The embodiment assigning to the two or more streams may be adopted, for example, in a microchip 150 for microparticle sorting. In this case, for example, two or more particle collection channels may be set up in the chip, or a branched flow channel may be used as the particle collection channel.

The microparticle sorting device according to the present technology may be a microparticle sorting device that generates droplets including microparticles, and sorts the microparticles by controlling the moving directions of the droplets. Examples of such a microparticle sorting device can include a flow cytometer. The flow cytometer may be either a flow-cell type or a jet-in-air-type. For example, the flow cytometer can be used as a microparticle sorting device according to the present technology by introducing a determination unit in accordance with the present technology into a normal flow cytometer. A common flow cytometer includes a light irradiation unit that irradiates, with light, microparticles flowing through a flow channel, a detection unit that detects light generated by the light irradiance, and a signal processing unit that generates information regarding the characteristics of the light. Therefore, for example, the sorting determination processing of microparticles by the determination unit according to the present technology can be performed with the use of the information regarding the characteristics of the light. By controlling the moving directions of the droplets including the microparticles, on the basis of the determination result obtained by the determination unit, a microparticle mixture (for example, a cell mixture) including multiple types of microparticles in specific particle constituent ratios is obtained.

A more specific example of the sorting process performed by the microparticle sorting device in accordance with the present technology will be described below.

(2) FIRST EXAMPLE OF FIRST EMBODIMENT (EXAMPLE OF MICROPARTICLE SORTING OPERATION)

In this example, a sorting process will be described for sorting, with the microparticle sorting device 100 according to the present technology, $CD4^+$ T cells and $CD8^+$ T cells, which are subsets of T cells, from a whole blood hemolyzed sample at a cell constituent ratio of 1:1.

Note that in this example and the following "(3) Second Example of First Embodiment (Example of Microparticle Sorting Operation)" and "(4) Third Example of First Embodiment (Example of Microparticle Sorting Operation)", cases of sorting two specific types of T cells is adopted for a better understanding of the present technology, but the operation of the microparticle sorting device 100 in these examples may sort cells other than the T cells and microparticles other than cells. Furthermore, an operation that is similar to the operation of the microparticle sorting device 100 according to the present example makes also it possible to sort three or more types of microparticles in predetermined particle constituent ratios. Furthermore, in these examples, cases of sorting at the particle constituent ratio of 1:1 are provided, but the operation of the microparticle sorting device 100 in this example makes also it possible to sort microparticles at other particle constituent ratios.

Figure 4A:
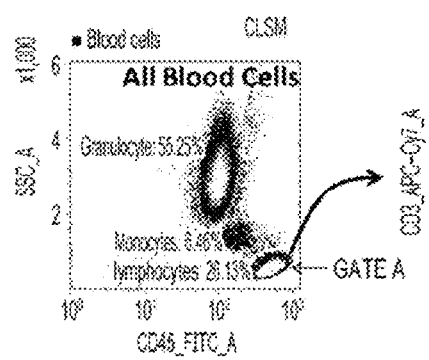
FIGS. 4A to 4C are diagrams showing examples of histograms obtained by making a test measurement with a microparticle sorting device with respect to a whole blood hemolyzed sample.
Figure 4B:
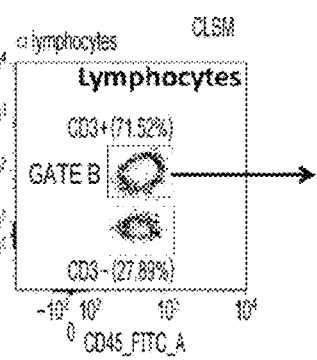
Figure 4C:
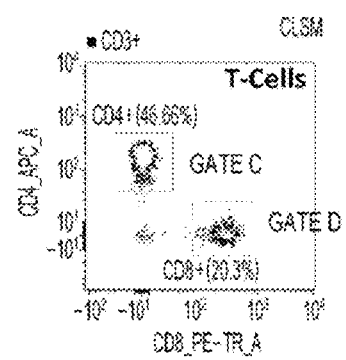

First, the user makes a test measurement with the microparticle sorting device 100 for the sample in which the whole blood is hemolyzed, and then obtains a histogram. A case is assumed where histograms as shown in FIGS. 4A to 4C are obtained as a result of the test measurement. In this case, the user sets a gate A so as to include a region corresponding to a lymphocyte in the histogram of FIG. 4A. Next, the user then expands gate A, thereby providing the histogram of FIG. 4B. The user sets a gate B so as to include a region corresponding to a lymphocyte which is $CD3^+$ (indicating T cells) in the histogram of FIG. 4B. Next, the user then expands the gate B, thereby providing the histogram of FIG. 4C. The user respectively sets gates C and D so as to include regions respectively corresponding to a $CD4^+$ T cell and a $CD8^+$ T cell, in the histogram of FIG. 4C. In other words, the cell in the gate A, in the gate B, and in the gate C is a $CD4^+$ T cell. Furthermore, the cell in the gate A, in the gate B, and in the gate D is a $CD8^+$ T cell.

As described above, the gates which should be set to sort target cells ($CD4^+$ T cells and $CD8^+$ T cells) are found by making the test measurement.

Note that among the cells in the gate B, the proportion of $CD4^+$ T cells (cells in the gate C) and the proportion of $CD8^+$ T cells (cells in the gate D) are respectively 46.66% and 20.3%. Therefore, even if cells are sorted in accordance with the or logic of "gate A and gate B and gate C" or "gate A and gate B and gate D", the cell constituent ratio between CD4+ T cells and CD8+ T cells in the sorted cell mixture will not be 1:1.

After the gates which should be set to sort target cells are found by the foregoing test measurement, the user specifies, for example, as shown in FIG. 5, gate logics as primary sorting criteria and particle constituent ratios for setting secondary sorting criteria. In FIG. 5, as primary sorting criteria, the gate logic of "gate A and gate B and gate C" is set for gate No. 1, and the gate logic of "gate A and gate B and gate D" is specified for gate No. 2. Moreover, in FIG. 5, the particle constituent ratio of 50% is specified for the gate No. 1, and the particle constituent ratio of 50% is specified for the gate No. 2. In other words, the particle constituent ratio between these two types of cells is specified to be 1:1.

After specifying the gate logics as primary sorting criteria is specified and the particle constituent ratios for setting the secondary sorting criteria, the microparticle sorting device according to the present technology starts a microparticle sorting process. The microparticle sorting process performed by the microparticle sorting device according to the present technology will be described below with reference to FIGS. 1 and 6. FIG. 1 is a diagram illustrating the configuration of the microparticle sorting device 100, as described above. FIG. 6 is a flow diagram for a microparticle sorting process in accordance with the present technology. The microparticle sorting process shown by the flow chart of FIG. 6 is a process of sorting only a predetermined number of cells that satisfy the gate logic of gate No. 1, and then sorting only a predetermined number of cells that satisfy the gate logic of gate No. 2. Details of the microparticle sorting process will be described below.

In a step S101 in FIG. 6, the user inputs the gate logic and the particle constituent ratio into the microparticle sorting device 100 via, for example, an interface.

The user who performs the input in the step S101 may be the same as or different from the user who specifies the gate logic, the primary sorting criteria as described above, and specifies the particle constituent ratio for setting the secondary sorting criteria. An example in which the users are different from each other may include a case of a development of a cell therapeutic agent and a manufacture of the cell therapeutic agent developed. The cell therapeutic agent may be developed, for example in a laboratory, and the gate logic and the particle constituent ratio may be set, for example, by specialists or engineers. The cell therapeutic agent developed may be manufactured, for example, in a plant by operators (who are other than the person performing the setting described above) of the microparticle sorting device.

Accompanying with the setting of the gate logic and the particle constituent ratio, a program for causing the microparticle sorting device to execute the microparticle sorting method according to the present technique may be prepared. The program may be transmitted, for example, by an information storage medium, or wirelessly or wiredly from the specialist or engineer to the operator.

In a step S102, the determination unit 105 sets the number of units for sorting. The number of units for sorting can be set by the determination unit 105, on the basis of, for example, the number of cells that satisfy each gate logic counted in the test measurement. Alternatively, the user may set the number of units for sorting, on the basis of the number of cells that satisfy each gate logic counted in the test measurement.

For example, as shown in FIG. 6, the number of units for sorting can be set to 100.

In a step S103, the determination unit 105 sets the acquired number of cells that satisfy the gate logic of gate No. 1 and the acquired number of cells that satisfy the gate logic of gate No. 2, on the basis of the particle constituent ratio specified by the user. These acquired numbers of cells can be set, on the basis of, for example, the unit number of units for sorting, set in the step S102, and on the particle constituent ratio. For example, the number of units for sorting is allocated to each gate in accordance with the particle constituent ratio.

For example, in a case where the number of units for sorting is set to 100 in the step S102, on the basis of the number of units (100) and the particle constituent ratio (1:1), the acquired number of cells that satisfy the gate logic of gate No. 1 is set to 50, and the acquired number of cells that satisfy the gate logic of gate No. 2 is set to 50.

In a step S104, the microparticle sorting device 100 starts the sorting process.

In a step S105, the microparticle sorting device 100 starts sorting cells that satisfy the gate logic of gate No. 1. For example, the control unit 103 drives a pump (not shown) for introducing the sample liquid and the sheath liquid respectively into the sample liquid channel 152 and the sheath liquid channel 154, thereby starting the sorting. The sample liquid and the sheath liquid are introduced by the driving into the sample liquid channel 152 and the sheath liquid channel 154, and then, these liquids merge at the merging part 162 to form a laminar flow. The laminar flow flows through the main flow channel 155 toward the sorting part 157.

In a step S106, the detection of light generated by irradiating, with light, cells flowing through the main flow channel 155 is performed. The detection is performed in the detection area 156. The light irradiation unit 101 performs the light irradiation, and the detection unit 102 detects the light generated by the light irradiation.

In a step S107, the determination unit 105 determines whether the light detected in the step S106 satisfies the gate logic of the gate No. 1. If the detected light satisfies the gate logic of gate No. 1, the control unit 103 proceeds with the process to a step S108. If the detected light fails to satisfy the gate logic of the gate No. 1, the control unit 103 returns the process to the step S106 to irradiate the next flowing cell with light, and detect the light generated by the light irradiation. The cells that have generated light that fails to satisfy the gate logic of gate No. 1 flow to the branched flow channel 158.

In the step S108, the determination unit 105 compares the number of cells already sorted into the particle sorting flow channel 159, which are determined to satisfy the gate logic of gate No. 1, with the acquired number of cells set in the step S103.

If the number of the sorted cells has not reached the acquired number of cells as a result of the comparison, the determination unit 105 determines that the cells determined to satisfy the gate logic of gate No. 1 in the step S107 are sorted. In response to the determination that the cells are sorted, the control unit 103 proceeds with the process to a step S109.

If the number of the sorted cells has reached the acquired number of cells as a result of the comparison, the determination unit 105 determines that the cells determined to satisfy the gate logic of gate No. 1 in the step S107 are not sorted. In response to the determination that the cells are not sorted, the control unit 103 proceeds with the process to a step S110.

In the step S109, the control unit 103 performs a process for sorting the cells determined to satisfy the gate logic of gate No. 1 in the step S107. For example, the sorting control unit 107 of the control unit 103 drives a piezo-electric actuator (not shown) provided on the particle sorting flow channel 159 after the lapse of a pre period of time after the passage of the cells through the detection area 156, thereby deforming the inside space of the particle sorting flow channel 159 to generate a negative pressure in the particle sorting flow channel 159. Thus, the cells are collected into the particle sorting flow channel 159.

In the step S110, the control unit 103 compares a value obtained by adding 1 to the current gate number with the maximum gate number.

If the value is equal to or smaller than the maximum gate number, the control unit 103 returns the process to the step S105, and the microparticle sorting device 100 starts to sort cells that satisfy the gate logic of the gate number obtained by adding 1 to the current gate number.

If the value is larger than the maximum gate number, the control unit 103 proceeds with the process to a step S111.

In the step S111, the control unit 103 determines whether the condition for ending the sorting process is satisfied or not. The condition for ending the sorting process can be, for example, whether the total of the acquired numbers of cells has reached a predetermined number or not, whether the period of time for which the sorting process has been performed has reached a predetermined value or not, whether the user inputs an instruction to end the sorting process or not (for example, whether a button for ending the sorting process has been clicked or not), or the like.

In a case where the condition for ending the sorting process is the total of the acquired numbers of cells has reached a predetermined number or not, the predetermined number may be specified in advance. For example, in a case where the predetermined number is 500, the number of units for sorting is 100, which is specified in step S102, and thus, in the fifth process of step S111 (in a case where the step S105 to the step S110 are repeated five times), the control unit 103 determines that the total of the acquired numbers of cells has reached the predetermined number.

If it is determined that the condition for ending the sorting process is satisfied, the control unit 103 proceeds with the process to a step S112.

If it is determined that the condition for ending the sorting process is not satisfied, the control unit 103 returns the process to the step S105 to start to sort cells. For example, the control unit 103 starts to sort cells that satisfy the gate logic of the smallest gate number.

The condition for ending the sorting process may be conditions other than those explained above. The condition for ending the sorting process may be, for example, whether or not it is detected that bubbles flow through the detection area 156. For example, a liquid-containing container for supplying the sample liquid or the sheath liquid is connected, for example, through a channel (a tube, and the like) to the sample liquid channel 152 or the sheath liquid channel 154. The liquid-containing container may include gas in addition to the sample liquid or the sheath liquid. When the liquid-containing container becomes nearly empty, the gas is turned into bubbles and they may flow through the sample liquid channel 152 or the sheath liquid channel 154 into the main flow channel 155. The length of the detection time of the light generated by irradiating, with light, the bubbles may be different from the length of the detection time of the light generated by irradiating, with light, the microparticles (in particular, longer). The characteristics of the light generated by irradiating, with light, the bubbles may also be different from the characteristics of the light generated by irradiating, with light, the microparticles. It is possible, consequently, to detect the flow of the bubbles on the basis of the difference. Then, the sorting process may be ended in accordance with the passage of the bubbles through the detection area 156 in the main flow channel 155.

Specifically, the light generated by irradiating, with light, the bubbles may be detected by the detection unit 102 (it is photoelectrically converted to an analog electrical signal), and the analog electrical signal may be converted into a digital electrical signal by the signal processing unit 104. Then, the determination unit 105 may determine whether the bubbles flow on the basis of the digital electrical signal. The control unit 103 may bring the sorting process to an end in accordance with the determination in which the bubbles flow through the detection area 156.

Alternatively, the condition for ending the sorting process may be whether it is detected that the bubbles pass through the predetermined position by the light irradiation to the predetermined position in the particle sorting flow channel 159 described above. In this case, as similar to the above, the light generated by irradiating with light is converted into a digital electrical signal by the detection unit and the signal processing unit, and the determination unit 105 may determine whether the bubbles pass through the predetermined position on the basis of the digital electrical signal. The control unit 103 may bring the sorting process to an end in accordance with the determination in which the bubbles pass through the predetermined position.

A further other example of the condition for ending the sorting process may be whether a weight of the liquid-containing container for supplying the sample liquid or the sheath liquid to the sample liquid channel 152 or the sheath liquid channel 154 reaches a predetermined value or less, or a decreased amount of the weight reaches a predetermined value or more. In order to weigh the liquid-containing container, a weight sensor may be connected to the microparticle sorting device 100. Amount data of the weight measured by the weight sensor are transmitted sequentially or continuously to the control unit 103, and the control unit 103 may bring the sorting process into an end in accordance with the amount data.

Alternatively, the sorting process weight condition may be whether the weight of the container connected to the particle sorting channel end 161 described above reaches a predetermined value or more, or an increased amount of the weight reaches a predetermined value or more. In order to weigh the container, a weight sensor may be connected to the microparticle sorting device 100. Amount data weighed by the weight sensor are transmitted sequentially or continuously to the control unit 103, and the control unit 103 may bring the sorting process into an end in accordance with the amount data.

In the step S112, the microparticle sorting device 100 ends the sorting process.

In accordance with the sorting process as mentioned above, $CD4^+$ T cells and $CD8^+$ T cells are collected at a cell constituent ratio of 1:1.

(3) SECOND EXAMPLE OF FIRST EMBODIMENT (EXAMPLE OF MICROPARTICLE SORTING OPERATION)

This example is another example of a sorting process for sorting, with the microparticle sorting device 100 according to the present technology, $CD4^+$ T cells and $CD8^+$ T cells, which are subsets of T cells, from a whole blood hemolyzed sample at a cell constituent ratio of 1:1.

First, the user makes a test measurement with the microparticle sorting device 100 for a sample in which the whole blood is hemolyzed, thereby finding the gates which should be set to sort target cells (CD4$^+$ T cells and CD8$^+$ T cells), as described in the foregoing "(2) First Example of First Embodiment (Example of Microparticle Sorting Operation)". In other words, the cell in the gate A, in the gate B, and in the gate C is a CD4$^+$ T cell. Furthermore, the cell in the gate A, in the gate B, and in the gate D is a CD8$^+$ T cell.

After the gates which should be set to sort target cells are found by the foregoing test measurement, the user specifies, for example, as shown in FIG. 5, gate logics as primary sorting criteria and particle constituent ratios for setting secondary sorting criteria. The gate logic and the particle constituent ratio are as described in the foregoing "(2) First Example of First Embodiment (Example of Microparticle Sorting Operation)".

After specifying the gate logics as primary sorting criteria is specified and the particle constituent ratios for setting the secondary sorting criteria, the microparticle sorting device according to the present technology starts a microparticle sorting process. The microparticle sorting process performed by the microparticle sorting device according to the present technology will be described below with reference to FIGS. 1 and 7. FIG. 1 is a diagram illustrating the configuration of the microparticle sorting device 100, as described above. FIG. 7 is a flow diagram for a microparticle sorting process in accordance with the present technology. The microparticle sorting process shown by the flow chart of FIG. 7 is a process of continuing a process of sorting cells that satisfy the gate logic of gate No. 1 and cells that satisfy the gate logic of gate No. 2, until the numbers of cells collected reach the acquired numbers set in advance for each cell. Details of the microparticle sorting process will be described below.

Steps S201 to S204 in FIG. 7 are the same as the steps S101 to S104 in FIG. 6. Therefore, descriptions of the steps S201 to S204 in FIG. 7 will be omitted.

In a step S205, the microparticle sorting device 100 starts sorting cells that satisfy either the gate logic of gate No. 1 or the gate logic of gate No. 2. For example, the control unit 103 drives a pump (not shown) for introducing the sample liquid and the sheath liquid respectively into the sample liquid channel 152 and the sheath liquid channel 154, thereby starting the sorting. The sample liquid and the sheath liquid are introduced by the driving into the sample liquid channel 152 and the sheath liquid channel 154, and then, these liquids merge at the merging part 162 to form a laminar flow. The laminar flow flows through the main flow channel 155 toward the sorting part 157.

In a step S206, the detection of light generated by irradiating, with light, cells flowing through the main flow channel 155 is performed. The detection is performed in the detection area 156. The light irradiation unit 101 performs the light irradiation, and the detection unit 102 detects the light generated by the light irradiation.

In a step S207, the determination unit 105 determines whether the light detected in the step S206 satisfies either the gate logic of the gate No. 1 or the gate logic of the gate No. 2. If the detected light satisfies any one of the gate logics, the control unit 103 proceeds with the process to a step S208. If the detected light fails to satisfy any of the gate logics, the control unit 103 returns the process to the step S206 to irradiate the next flowing cell with light, and detect the light generated by the light irradiation. The cells that have generated light that fails to satisfy any of the gate logics flow to the branched flow channel 158.

In the step S208, the determination unit 105 determines whether the cells that have generated light that satisfies either the gate logic of the gate No. 1 or the gate logic of the gate No. 2 should be sorted. The determination is performed as follows.

If the detected light satisfies the gate logic of the gate No. 1, the number of cells already sorted into the particle sorting flow channel 159, which are determined to satisfy the gate logic of gate No. 1, is compared with the acquired number of cells set in the step S203. If the number of the sorted cells has not reached the acquired number of cells as a result of the comparison, the determination unit 105 determines that the cells determined to satisfy the gate No. 1 in the step S207 are sorted. In response to the determination that the cells are sorted, the control unit 103 proceeds with the process to a step S209. If the number of the sorted cells has reached the acquired number of cells as a result of the comparison, the determination unit 105 determines that the cells determined to satisfy the gate No. 1 in the step S207 are not sorted. In response to the determination that the cells are not sorted, the control unit 103 proceeds with the process to a step S210.

If the detected light satisfies the gate logic of the gate No. 2, the number of cells already sorted into the particle sorting flow channel 159, which are determined to satisfy the gate logic of gate No. 2, is compared with the acquired number of cells set in the step S203. If the number of the sorted cells has not reached the acquired number of cells as a result of the comparison, the determination unit 105 determines that the cells determined to satisfy the gate No. 2 in the step S207 are sorted. In response to the determination that the cells are sorted, the control unit 103 proceeds with the process to a step S209. If the number of the sorted cells has reached the acquired number of cells as a result of the comparison, the determination unit 105 determines that the cells determined to satisfy the gate No. 2 in the step S207 are not sorted. In response to the determination that the cells are not sorted, the control unit 103 proceeds with the process to a step S210.

In the step S209, the control unit 103 performs a process for sorting the cells determined to satisfy either the gate logic of gate No. 1 or the gate logic of gate No. 2 in the step S207. For example, the sorting control unit 107 of the control unit 103 drives a piezo-electric actuator (not shown) provided on the particle sorting flow channel 159 after the lapse of a pre period of time after the passage of the cells through the detection area 156, thereby deforming the inside space of the particle sorting flow channel 159 to generate a negative pressure in the particle sorting flow channel 159. Thus, the cells are collected into the particle sorting flow channel 159.

The control unit 103 may return the process to the step S206 after the process of the step S209. Alternatively, the control unit 103 may perform the process of the step S206 before the process of the step S209 is completed. Thus, even in a case where the interval is narrow between cells aligned in the laminar flow, the sorting process can be performed for continuous cells.

In the step S210, the control unit 103 determines, for all of gate numbers, whether the number of cells already sorted into the particle sorting flow channel 159 has reached the acquired number of cells, set in the step S203, or not. If the number of cells already sorted into the particle sorting flow channel 159 has reached the acquired number of cells, set in the step S203 for all of the gate numbers, the control unit 103 proceeds with the process to a step S211. If the number of cells already sorted into the particle sorting flow channel 159 has not reached the acquired number of cells, set in the step S203 for at least one of the gate numbers, the control unit returns the process to the step S206 to continue the cell sorting process.

In the step S211, the control unit 103 determines whether the condition for ending the sorting process is satisfied or not. The condition for ending the sorting process can be, for example, whether the total of the acquired numbers of cells has reached a predetermined number or not, whether the period of time for which the sorting process has been performed has reached a predetermined value or not, whether the user inputs an instruction to end the sorting process or not (for example, whether a button for ending the sorting process has been clicked or not), or the like.

If it is determined that the condition for ending the sorting process is satisfied, the control unit 103 proceeds with the process to a step S212.

If it is determined that the condition for ending the sorting process is not satisfied, the control unit 103 returns the process to the step S205 to start to sort cells.

In the step S212, the microparticle sorting device 100 ends the sorting processing.

In accordance with the sorting process as mentioned above, CD4$^+$ T cells and CD8$^+$ T cells are collected at a cell constituent ratio of 1:1.

Also, when the sorting process described above is performed, it is possible to perform the sorting in the number of units. In the explanation above, the number of units is set to 100, but the number of units is not limited thereto, and it may be set depending on the number of cells to be sorted. The number of units may be, for example, 10-1000000, particularly 50-100000, more particularly 100-10000. When the sorting in the number of units are repeated, a microparticle mixture including two or more different microparticle populations can be efficiently prepared in a predetermined particle constituent ratio.

In one preferable embodiment of the present technology, the steps S205 to S212 above are repeated; in other words, the sorting is repeated in the number of units. For example, a case where the number of units is 10000, four gate logics (gates A, B, C, and D) are set, and the particle constituent ratio is A:B:C:D=1:2:3:4 is supposed. In this case, when the sorting process is performed in the number of units, cell mixtures including 1000, 2000, 3000, and 4000 cells satisfying the gate logics A, B, C, and D, respectively. Cell mixtures obtained by repeating the sorting process in the number of units 10 times include 100000 cells, and the particle constituent ratio of the 100000 cells is A:B:C:D=1:2:3:4. When the sorting process is performed as described above, microparticle mixtures having a predetermined particle constituent ratio can be efficiently obtained.

Note that the repeating of the sorting process in the number of units may be performed in "(2) First Example of First Embodiment (Example of Microparticle Sorting Operation)" described above, and in "(4) Third Example of First Embodiment (Example of Microparticle Sorting Operation)" described below, not limited to this case.

(4) THIRD EXAMPLE OF FIRST EMBODIMENT (EXAMPLE OF MICROPARTICLE SORTING OPERATION)

This example is an example of sorting, with the microparticle sorting device 100 according to the present technology, CD4$^+$ T cells and CD8$^+$ T cells which are subsets of T cells, from a whole blood hemolyzed sample, such that the constituent ratio between the cells falls within a predetermined numerical range including a ratio of 1:1 specified by the user.

First, the user makes a test measurement with the microparticle sorting device 100 for a sample in which the whole blood is hemolyzed, thereby finding the gates which should be set to sort target cells (CD4$^+$ T cells and CD8$^+$ T cells), as described in the foregoing "(2) First Example of First Embodiment (Example of Microparticle Sorting Operation)". In other words, the cell in the gate A, in the gate B, and in the gate C is a CD4$^+$ T cell. Furthermore, the cell in the gate A, in the gate B, and in the gate D is a CD8$^+$ T cell.

After the gates which should be set to sort target cells are found by the foregoing test measurement, the user specifies, for example, as shown in FIG. 5, gate logics as primary sorting criteria and particle constituent ratios for setting secondary sorting criteria. The gate logic and the particle constituent ratio are as described in the foregoing "(2) First Example of First Embodiment (Example of Microparticle Sorting Operation)".

After specifying the gate logics as primary sorting criteria is specified and the particle constituent ratios for setting the secondary sorting criteria, the microparticle sorting device according to the present technology starts a microparticle sorting process. The microparticle sorting process performed by the microparticle sorting device according to the present technology will be described below with reference to FIGS. 1 and 8. FIG. 1 is a diagram illustrating the configuration of the microparticle sorting device 100, as described above. FIG. 8 is a flow diagram for a microparticle sorting process in accordance with the present technology. The microparticle sorting process shown by the flow chart of FIG. 8 is, a process of firstly acquiring predetermined numbers of cells, for example, by performing a sorting process such as the process described in the foregoing "(2) First Example of First Embodiment (Example of Microparticle Sorting Operation)" or "(3) Second Example of First Embodiment (Example of Operation of Sorting Microparticles)", and then sorting particles as long as the constituent ratios for each cell fall within a predetermined numerical range including the ratio specified by the user. Details of the microparticle sorting process will be described below.

In a step S301 in FIG. 8, the user inputs the gate logic and the particle constituent ratio into the microparticle sorting device 100 via, for example, an interface.

In a step S302, the microparticle sorting device 100 starts the sorting process.

In a step S303, the microparticle sorting device 100 acquires cells that satisfy the gate logic of the gate No. 1 and cells that satisfy the gate logic of gate No. 2 such that the constituent ratio between the cells is the particle constituent ratio specified by the user. For the acquisition, for example, the sorting process is performed which is described in the foregoing "(2) First Example of First Embodiment (Example of Microparticle Sorting Operation)" or "(3) Second Example of First Embodiment (Example of Operation of Sorting Microparticles)".

For example, as shown in FIG. 8, the number of units for sorting is set to 100. Then, among the 100 cells, the acquired number of cells that satisfy the gate logic of the gate No. 1 is set to 50, and the acquired number of cells that satisfy the gate logic of the gate No. 2 is set to 50. In order to achieve these acquired numbers, for example, the process of the steps S104 to S110 or the process of the steps S204 to S210 can be performed.

The above-described sorting process collects 50 cells that satisfy the gate logic of the gate No. 1 and 50 cells that satisfy the gate logic of the gate No. 2.

In a step S304 and subsequent steps, the microparticle sorting device 100 continues the microparticle sorting process. In the step S304 and the subsequent steps, a process of sorting particles as long as the constituent ratios of the respective cells fall within a predetermined numerical range including the ratio specified by the user is performed.

In a step S304, the detection of light generated by irradiating, with light, cells flowing through the main flow channel 155 is performed. The detection is performed in the detection area 156. The light irradiation unit 101 performs the light irradiation, and the detection unit 102 detects the light generated by the light irradiation.

In a step S305, the determination unit 105 determines whether the light detected in the step S304 satisfies either the gate logic of the gate No. 1 or the gate logic of the gate No. 2. If the detected light satisfies any one of the gate logics, the control unit 103 proceeds with the process to a step S306. If the detected light fails to satisfy any of the gate logics, the control unit 103 returns the process to the step S304 to irradiate the next flowing cell with light, and detect the light generated by the light irradiation. The cells that have generated light that fails to satisfy any of the gate logics flow to the branched flow channel 158.

In the step S306, the determination unit 105 determines whether the particle constituent ratio in the case of sorting cells that generate the light determined to satisfy either the gate logic of gate No. 1 or the gate logic of gate No. 2 (that is, any of the primary sorting criteria) in the step S305 falls within a predetermined numerical range including the ratio specified by the user or not.

For example, (the ratio threshold value specified by the user)±(threshold value) can be adopted as the predetermined numerical range. In this example, the particle constituent ratios for each cell are each 50%. Therefore, in the present example, 50%±0.05% (that is, 49.5% to 50.5%) is the predetermined numerical range in a case where 1% is set as the threshold value.

As a result of the determination, if the particle constituent ratio in the case of sorting cells that generate the light determined to satisfy any of the primary sorting criteria falls within the predetermined numerical range, the control unit 103 proceeds with the process to a step S307.

As a result of the determination, if the particle constituent ratio in the case of sorting cells that generate the light determined to satisfy any of the primary sorting criteria fails to fall within the predetermined numerical range, the control unit 103 proceeds with the process to a step S308.

In the step S307, the control unit 103 performs a process for sorting cells that generate light that satisfies either the gate logic of gate No. 1 or the gate logic of gate No. 2 in the step S305. For example, the sorting control unit 107 of the control unit 103 drives a piezo-electric actuator (not shown) provided on the particle sorting flow channel 159 after the lapse of a pre period of time after the passage of the cells through the detection area 156, thereby deforming the inside space of the particle sorting flow channel 159 to generate a negative pressure in the particle sorting flow channel 159. Thus, the cells are collected into the particle sorting flow channel 159.

The control unit 103 may return the process to the step S304 after the process of the step S307. Alternatively, the control unit 103 may perform the process of the step S304 before the process of the step S307 is completed. Thus, even in a case where the interval is narrow between cells aligned in the laminar flow, the sorting process can be performed for continuous cells.

In the step S308, the control unit 103 determines whether the condition for ending the sorting process is satisfied or not. The condition for ending the sorting process can be, for example, whether the total of the acquired numbers of cells has reached a predetermined number or not, whether the period of time for which the sorting process has been performed has reached a predetermined value or not, whether the user inputs an instruction to end the sorting process or not (for example, whether a button for ending the sorting process has been clicked or not), or the like.

If it is determined that the condition for ending the sorting process is satisfied, the control unit 103 proceeds with the process to a step S309.

If it is determined that the condition for ending the sorting process is not satisfied, the control unit 103 returns the process to the step S304 to continue to sort cells.

In the step S309, the microparticle sorting device 100 ends the sorting processing.

After fifty $CD4^+$ T cells and fifty $CD8^+$ T cells are each collected in the sorting process as described above, the cell sorting process is further continued as long as the cell constituent ratio falls within the predetermined numerical range. Therefore, more cells can be sorted in constituent ratios within the predetermined numerical range.

(5) FOURTH EXAMPLE OF FIRST EMBODIMENT (EXAMPLE OF PARTICLE SORTING PROCESS WITH CONNECTED MICROCHIPS FOR MICROPARTICLE SORTING)

Various objects can be achieved by applying the present technology to a microparticle sorting process performed by a flow channel unit for microparticle sorting with connected microchips for microparticle sorting. A sorting process performed by a microparticle sorting device including the flow channel unit for microparticle sorting will be described below.

(5-1) Configuration Example of Microparticle Sorting Device

The microparticle sorting device according to the present technology, including the channel unit for microparticle sorting, will be described below with reference to FIG. 9.

FIG. 9 is a diagram illustrating a configuration example of a microparticle sorting device 900 according to the present technology. As shown in FIG. 9, the microparticle sorting device 900 according to the present technology includes a light irradiation unit 101a, a detection unit 102a, and a microchip 150a for microparticle sorting, and a light irradiation unit 101b, a detection unit 102b, and a microchip 150b for microparticle sorting. The microparticle sorting device 900 further includes a control unit 103. The control unit 103, which may be the same as that shown in FIG. 1, includes a signal processing unit 104, a determination unit 105, and a sorting control unit 107.

The light irradiation unit 101a irradiates, with light, microparticles flowing through a flow channel in the microchip 150a for microparticle sorting. The detection unit 102a detects light generated by the light irradiation. Depending on the characteristics of the light detected by the detection unit 102a, the control unit 103 controls the flow in the microchip

150a for microparticle sorting, thereby only sorting the microparticles to be collected.

The light irradiation unit 101b, the detection unit 102b, and the microchip 150b for microparticle sorting also perform a microparticle sorting process in a similar manner to the light irradiation unit 101a, the detection unit 102a, and the microchip 150a for microchip sorting.

The light irradiation units 101a and 101b are the same as the light irradiation unit 101 described in the foregoing "(1) Description of First Embodiment". The detection units 102a and 102b are the same as the detection unit 102 described in the foregoing "(1) Description of First Embodiment". The microchips 150a and 150b for microparticle sorting are the same as the microchip 150 for microparticle sorting, described in the foregoing "(1) Description of First Embodiment". The control unit 103 and the components included therein are also the same as described above in foregoing "(1) Description of First Embodiment". Therefore, the contents described in the foregoing "(1) Description of First Embodiment" apply to these components, descriptions of these components will be omitted.

Note that the light irradiation units 101a and 101b are regarded as the same unit in this example, but may be different. Similarly, the detection units 102a and 102b may be regarded as the same unit, or may be different units. The microchips 150a and 150b for microparticle sorting may be also regarded as the same unit, or may be different units.

A particle sorting channel end 161a of the microchip 150a for microparticle sorting and a sample liquid inlet 151b of the microchip 150b for microparticle sorting are connected by a flow channel connecting member 901. Further, a fluid storage container 902 is provided between a sorting part 157a of the microchip 150a for microparticle sorting and a sorting part 157b of the microchip 150b for microparticle sorting. The fluid storage container 902 is configured such that the fluid storage amount in the container varies in accordance with the difference in flow rate between before and after the container. A pump 903 is provided downstream of the fluid storage container 902 and upstream of the sorting part 157b of the microchip 150b for microparticle sorting.

The flow channel connecting member 901 may be, for example, a tube and the like. The material of the flow channel connecting member 901 may be selected appropriately by those skilled in the art, from those used in the technical field to which the present technology belongs. The flow channel connecting member 901 may be, for example, a polyvinyl chloride (PVC) tube, a silicone tube, a polyetheretherketone (PEEK) tube, a polytetrafluoroethylene (PTFE) tube, or a thermoplastic elastomer tube, or may have multiple types of tubes connected.

The fluid storage container 902 is provided on the flow channel connecting the two sorting parts 157a and 157b. More specifically, the container 902 is provided on the flow channel connecting the two sorting parts 157a and 157b such that the fluid is capable of flowing from the flow channel connecting the two sorting parts 157a and 157b. The container is provided, thereby making it possible to control the flow rate of the fluid flowing from the sorting part 157a of the upstream microchip 150a for microparticle sorting into the container 902 and the flow rate of the fluid flowing from the container 902 into the sorting part 157a of the downstream microchip 150b for microparticle sorting independently of each other. In other words, the flow rate in the flow channel located upstream of the container 902 and downstream of the sorting part 157a of the microchip 150a for microparticle sorting, and the flow rate in the flow channel located downstream of the container 902 and upstream of the sorting part 157b of the microchip 150b for microparticle sorting can be controlled independently of each other.

For example, the fluid storage container 902 can suppress the influence on the flow rate in the flow channel downstream of the fluid storage container 902 due to the flow rate fluctuation in the flow channel upstream of the fluid storage container 902, or the influence on the flow rate in the flow channel upstream of the fluid storage container 902 due to the flow rate fluctuation in the flow channel downstream of the fluid storage container 902. The flow rate variation can be, for example, a pulsating flow derived from pump driving or a pulsating flow derived from the microparticle sorting process.

In a case where the flow rate upstream of the fluid storage container 902 is not consistent with the flow rate downstream of the fluid storage container 902, the fluid storage container 902 changes its fluid storage amount in accordance with the difference between the two flow rates. Even under the condition in which these two flow rates are not consistent due to the change in fluid storage amount, microparticle sorting in each of the two microchips 150a and 150b for microparticle sorting can be performed under flow rate conditions that are independent of each other.

The fluid storage container 902 may be configured such that a liquid-air interface is formed in the container. The fluid storage container in which the liquid-air interface is formed is suitable for suppressing the influence of the flow rate variation caused by the microparticle sorting operation in each of the upstream sorting part 157a and the downstream sorting part 157b. For example, a pulsating flow can be dispersed or absorbed by the fluid storage container in which the liquid-air interface is formed. The fluid storage container 902 can function as a component for dispersing or absorbing the pulsating flow.

The fluid storage container 902 may be configured to expand, for example, with change (increase) in fluid storage amount. The fluid storage container 902 may be configured to expand depending on the structure of the fluid storage container 902, or may be configured to expand depending on the material characteristics (in particular, elastic characteristics) of the fluid storage container 902.

In accordance with one embodiment of the present technology, the fluid storage container 902 itself may include a material that has no elastic characteristics. According to this embodiment, the fluid storage container 902 may be configured to be capable of expanding depending on the structure of the container. According to this embodiment, the fluid storage container 902 may be configured to, for example, have the form of a sheet in the case of storing no fluid, and increase the inner volume of the fluid storage container 902 (like, for example, a plastic bag, an infusion bag, or the like) as the fluid is stored.

In accordance with another embodiment of the present technology, the fluid storage container 902 may include a material that has elastic characteristics (for example, a rubber material or the like). According to this embodiment, the fluid storage container itself expands (for example, expands like a balloon or the like), thereby making it possible to store more fluid therein.

The fluid storage container 902 may have gas (for example, air or inert gas such as nitrogen gas and argon gas) encapsulated in advance. The gas can be compressed as the fluid is stored in the fluid storage container.

The fluid storage container 902 may have a filter provided therein. The filter can be intended, for example, for preventing contamination derived from the outside air. The filter may be, for example, capable of being communicating the pressure (for example, air pressure or the like) of the gas inside the fluid storage container with the outside air. The filter may include a material that is impermeable to liquid.

For example, in a case where the flow rate upstream of the fluid storage container 902 is higher than the flow rate downstream of the fluid storage container 902, an amount of liquid corresponding to the difference between these two flow rates flows into the fluid storage container 902 and the fluid storage container 902 expands according to the inflow. Thus, the flow rate of the sample liquid introduced into the sample liquid inlet 151*b* of the microchip 150*b* for microparticle sorting is a flow rate as controlled by the pump 903, without being affected by the flow rate upstream of the fluid storage container 902.

Furthermore, for example, in a case where the flow rate upstream of the fluid storage container 902 is lower than the flow rate downstream of the fluid storage container 902, an amount of liquid corresponding to the difference between these two flow rates flows out of the fluid storage container 902. In this case, for example, a predetermined amount of liquid may be contained in the fluid storage container 902 in advance. The liquid flows out downstream of the fluid storage container 902 in accordance with the difference between the two flow rates. Accordingly, the flow rate upstream of the fluid storage container 902 is not affected by the flow rate downstream of the fluid storage container 902.

Furthermore, the fluid storage container 902 may be configured such that the fluid, in particular, the liquid flowing into the container, is not leaked from the container.

The material of the fluid storage container 902 can be material that enables such change in fluid storage amount and retention of fluid. The material may be selected appropriately by those skilled in the art. The container 902 may be, for example, a plastic bag. The plastic bag may be, for example, a bag made from polyethylene, polypropylene, polyvinyl chloride, or ethylene vinyl acetate copolymer.

The pump 903 can be, for example, but not limited to, a peristaltic pump (tube pump), a roller pump, a syringe pump, or a centrifugal pump. The pump can preferably be a peristaltic pump or a roller pump for more precise control of the flow rate.

The fluid storage container 902 can absorb the pulsating flow generated as the pump 903 is driven. Therefore, it is possible to eliminate or reduce the influence of the pulsating flow on the flow rate in the microchip 150*a* for microparticle sorting, upstream of the fluid storage container 902.

(5-2) Example of Sorting Process

According to one embodiment of the present technology, in the upstream microchip 150*a* for microparticle sorting, microparticle sorting is performed in accordance with the or logic provided in a common flow cytometer, and next, the microparticle sorting process according to the present technology is performed in the downstream microchip 150*b* for microparticle sorting.

In the embodiment, the purity for multiple types of target microparticles is increased by the microparticle sorting with the upstream microchip 150*a* for microparticle sorting. The sorting is, however, based on the or logic, and the constituent ratios of the multiple types of target microparticles are thus not changed before or after the microparticle sorting.

In the microparticle sorting with the downstream microchip 150*b* for microparticle sorting, the microparticle sorting process in accordance with the present technology is performed, thus making it possible to collect the multiple types of target microparticles at the particle constituent ratio specified by the user.

(5-3) Another Example of Sorting Process

In accordance with another embodiment of the present technology, the microparticle sorting process in accordance with the present technology is performed in both the upstream microchip 150*a* for microparticle sorting and the downstream microchip 150*b* for microparticle sorting.

According to this embodiment, the microparticle sorting process in accordance with the present technology is performed in both the upstream microchip 150*a* for microparticle sorting and the downstream microchip 150*b* for microparticle sorting, thus making it possible to collect the multiple types of target microparticles at the particle constituent ratio specified by the user. Moreover, the number of microparticles supplied to the downstream microchip 150*b* for microparticle sorting is smaller than that in the case of the foregoing "(5-2) Example of Sorting Process", thus further increasing the purity of the target microparticles.

2. SECOND EMBODIMENT (CELL THERAPEUTIC AGENT MANUFACTURING DEVICE)

The cell therapeutic agent manufacturing device in accordance with the present technology includes a determination unit that determines whether cells are sorted, on the basis of light generated by irradiating, with light, the cells flowing through a flow channel, and a cell sorting part for sorting the cells determined to be sorted by the determination unit.

The determination unit performs a primary sorting determination to determine, on the basis of characteristics of the light, whether the cells belong to any one of two or more different cell populations are sorted, and then performs a secondary sorting determination to determine whether the cells determined to belong to any one of the cell populations in the primary sorting determination are sorted, on the basis of a cell constituent ratio specified for the two or more different cell populations, and the cells sorted by the cell sorting part are collected in one container.

The determination unit is considered as described in the foregoing "1. First Embodiment (Microparticle Sorting Device)", and the description also applies to the present embodiment. The cell therapeutic agent manufacturing device in accordance with to the present technology includes the determination unit, thus making it possible to sort the multiple types of cell populations at in specified constituent ratios.

The cell therapeutic agent manufacturing device in accordance with to the present technology further includes the cell sorting part for sorting cells determined to be sorted by the determination unit, and cells sorted by the cell sorting part are collected in one container.

The cell sorting part can be the same as the sorting part described in the foregoing "1. First Embodiment (Microparticle Sorting Device)". For example, the cell sorting part can include a cell sorting flow channel for sorting cells determined to be sorted by the determination unit, and a branched flow channel for flowing cells determined not to be sorted.

The cells sorted by the cell sorting part are collected in one container. Therefore, the multiple types of cells collected are present in the container at the specified composition ratio.

As described above, in the container, multiple types of cell populations are collected at the specified constituent ratio. Therefore, the cell therapeutic agent manufacturing device in accordance with to the present technology can manufacture, in a simple manner, a cell therapeutic agent including multiple types of cell populations at a constituent ratio that is suitable for treating a certain disease. The types and constituent ratios of cells sorted by the cell therapeutic agent manufacturing device in accordance with to the present technology may be appropriately selected by those skilled in the art, depending on the target disease.

In the present technology, the term of cell therapy means the prevention or procedure (covering treatment and alleviation) of a target disease or injury by the administration of autologous, allogeneic or xenogeneic cells processed or modified in vitro to a subject (for example, a mammal, particularly a primate, more particularly a human). In the present technology, the cell therapeutic agent can be a drug for use in cell therapy. The cell therapeutic can include autologous, allogeneic, or xenogeneic cells processed or modified in vitro as mentioned above. For example, the cells included in cell therapeutic agents can include, for example, stem cells (for example, mesenchymal stem cells, adipose stem cells, ES cells, iPS cells, and the like), immune system cells (for example, lymphocytes and the like), and chondrocytes, and cells derived from any of the cells.

A configuration example of a cell therapeutic agent manufacturing device according to the present technology is shown in FIG. 10. As shown in FIG. 10, the cell therapeutic agent manufacturing device 1000 according to the present technology includes a light irradiation unit 101, a detection unit 102, a control unit 103, and a microchip 150 for microparticle sorting. The light irradiation unit 101, the detection unit 102, the control unit 103, and the microchip 150 for microparticle sorting are all considered as described in the foregoing "1. First Embodiment (Microparticle Sorting Device)", and the description also applies to the present configuration example. The determination unit included in the control unit 103 can perform the microparticle sorting process according to the present technology. Thus, multiple types of cells can be sorted in specified constituent ratios.

The microchip 150 for microparticle sorting has a particle sorting channel end 161 connected to one end of a tube 180, and the tube 180 has multiple ends connected to a container 181. Thus, multiple types of cells sorted into a particle sorting flow channel 159 are collected through the tube 180 into a container 181. The multiple types of cells are sorted at a constituent ratio indicated as mentioned above. Therefore, the multiple types of cells collected in the container 181 are present at the specified composition ratio. The specified constituent ratio is made suitable for procedure of a certain disease, thereby making it possible to provide, as a cell therapeutic drug product, the container 181 containing the multiple types of cells at the specified constituent ratio as it is to a patient.

3. THIRD EMBODIMENT (MICROPARTICLE SORTING METHOD)

The microparticle sorting method in accordance with the present technology includes a sorting determination step of determining whether microparticles are sorted, on the basis of light generated by irradiating, with light, the microparticles flowing through a flow channel. The sorting determination unit step includes a primary sorting determination step of determining, on the basis of characteristics of the light, whether the microparticles belong to any one of two or more different microparticle populations, and a secondary sorting determination step of determining, whether the microparticles determined to belong to any one of the microparticle populations in the primary sorting determination step are sorted, on the basis of the particle constituent ratio specified for the two or more different microparticle populations.

The details of the primary sorting determination step and secondary sorting determination step are considered as described in "(1-1) Primary Sorting Determination" and "(1-2) Secondary Sorting Determination" of 1. mentioned above, and the descriptions thereof will be thus omitted.

The microparticle sorting method in accordance with the present technology includes the sorting determination step, thereby making it possible to sort multiple types of microparticles in specified constituent ratios.

An example of the flow chart for the microparticle sorting method in accordance with the present technology is considered as shown in FIG. 6 described in "(2) First Example of First Embodiment (Example of Microparticle Sorting Operation)" in 1. mentioned above. The step S107 in FIG. 6 corresponds to the primary sorting determination step. The step S108 in FIG. 6 corresponds to the secondary sorting determination step. The step S107 and the step S108 are considered as described in "(2) First Example of First Embodiment (Example of Microparticle Sorting Operation)" in 1. mentioned above, and the descriptions thereof will be thus omitted.

The microparticle sorting method in accordance with the present technology can include the steps shown in FIG. 6, other than the steps S107 and S108. These steps are considered as described in "(2) First Example of First Embodiment (Example of Microparticle Sorting Operation)" in 1. mentioned above, and the descriptions thereof will be thus omitted.

Another example of the flow chart for the microparticle sorting method in accordance with the present technology is considered as shown in FIG. 7 described in "(3) Second Example of First Embodiment (Example of Microparticle Sorting Operation)" in 1. mentioned above. The step S207 in FIG. 7 corresponds to the primary sorting determination step. The step S208 in FIG. 7 corresponds to the secondary sorting determination step. The step S207 and the step S208 are considered as described in "(3) Second Example of First Embodiment (Example of Microparticle Sorting Operation)" in 1. mentioned above, and the descriptions thereof will be thus omitted.

The microparticle sorting method in accordance with the present technology can include the steps shown in FIG. 7, other than the steps S207 and S208. These steps are considered as described in "(3) Second Example of First Embodiment (Example of Microparticle Sorting Operation)" in 1. mentioned above, and the descriptions thereof will be thus omitted.

Yet another example of the flow chart for the microparticle sorting method in accordance with the present technology is considered as shown in FIG. 8 described in "(4) Third Example of First Embodiment (Example of Microparticle Sorting Operation)" in 1. mentioned above. The step S305 in FIG. 8 corresponds to the primary sorting determination step. The step S306 in FIG. 8 corresponds to the secondary sorting determination step. The step S305 and the step S306 are considered as described in "(4) Third Example of First Embodiment (Example of Microparticle Sorting Operation)" in 1. mentioned above, and the descriptions thereof will be thus omitted.

Furthermore, in the step S303 in FIG. 8, the sorting process is performed which is described in the foregoing "(2) First Example of First Embodiment (Example of Microparticle Sorting Operation)" or "(3) Second Example of First Embodiment (Example of Operation of Sorting Microparticles)". Among the steps performed in these sorting processes, the steps S107 and S108 and the steps S207 and S208 correspond to the primary sorting determination step and the secondary sorting determination step, as described above.

The microparticle sorting method in accordance with the present technology can include the steps shown in FIG. 9, other than the steps S305 and S306. These steps are considered as described in "(4) Third Example of First Embodiment (Example of Microparticle Sorting Operation)" in 1. mentioned above, and the descriptions thereof will be thus omitted.

The present technology also provides a program for causing the microparticle sorting device (particularly the microparticle sorting device according to the present technology) or the control unit thereof, or the cell therapeutic agent manufacturing device (particularly the cell therapeutic agent manufacturing device according to the present technology) or the control unit thereof to execute the microparticle sorting method according to the present technology.

Specifically, the program causes the microparticle sorting device (particularly the microparticle sorting device according to the present technology) or the control unit thereof, or the cell therapeutic agent manufacturing device (particularly the cell therapeutic agent manufacturing device according to the present technology) or the control unit thereof to execute the sorting determination step of determining whether the microparticles are sorted on the basis of the light generated by irradiating, with light, the microparticles flowing through the flow channel. The sorting determination step includes a primary sorting determination step of determining, on the basis of the characteristics of the light, whether the microparticles belong to any one of two or more different microparticle populations; and a secondary sorting determination step of determining, whether the microparticles determined to belong to any one of the microparticle populations in the primary sorting determination step are sorted, on the basis of the particle constituent ratio specified for the two or more different microparticle populations. These steps are as explained above, and the explanations are omitted.

The program may be stored, for example, on an information storage medium such as an SD card, a microSD card, an USB memory, a CD, or a DVD. Otherwise, the program may be stored in a storage unit provided in the microparticle sorting device (particularly the microparticle sorting device according to the present technology) or the cell therapeutic agent manufacturing device (particularly the cell therapeutic agent manufacturing device according to the present technology).

Note that the present technology can also be configured as follows.

[1] A microparticle sorting device comprising circuitry configured to: obtain optical information indicating a first microparticle population and a second microparticle population; and control, based on at least one constituent amount for the first microparticle population and the second microparticle population, sorting of a first group of microparticles belonging to the first microparticle population and a second group of microparticles belonging to the second microparticle population to obtain a mixture of microparticles including microparticles both from the first microparticle population and the second microparticle population.

[2] The microparticle sorting device of [1], wherein the circuitry is further configured to control sorting of microparticles based on light from the microparticles detected in response to irradiating the microparticles with excitation light as the microparticles flow through a flow channel.

[3] The microparticle sorting device of [2], wherein the circuitry is further configured to determine, based on at least one characteristic of the detected light and the optical information, the first group of microparticles as belonging in the first microparticle population and the second group of microparticles as belonging in the second microparticle population.

[4] The microparticle sorting device of [3], wherein the at least one characteristic includes a feature of fluorescent light and/or scattered light.

[5] The microparticle sorting device of any one of [1] to [4], further comprising a microchip configured to perform the sorting of the first group of microparticles and the second group of microparticles. [6] The microparticle sorting device of [5], wherein the microchip comprises a particle collection channel configured to transport the mixture of microparticles into a container.

[7] The microparticle sorting device of [6], wherein the microchip further comprises a main flow channel through which a fluid including microparticles of the first microparticle population and of the second microparticle population flows, and a branched flow channel connected to the main flow channel, wherein the particle collection channel is coaxial with the main flow channel.

[8] The microparticle sorting device of any one of [1] to [7], wherein the mixture of microparticles is collected in a container.

[9] The microparticle sorting device of any one of [1] to [8], wherein the at least one constituent amount includes a range of constituent ratios of the first microparticle population to the second microparticle population, and controlling sorting of the first group of microparticles and the second group of microparticles further comprises obtaining the mixture of microparticles to have a ratio of the first microparticle population to the second microparticle population within the range of constituent ratios.

[10] The microparticle sorting device of [9], wherein controlling sorting of the first group of microparticles and the second group of microparticles further comprises: controlling sorting of a first microparticle in the first group to not include the first microparticle in the mixture of microparticles in response to determining that the mixture of microparticles has a ratio of the first microparticle population to the second microparticle population within the range of constituent ratios; and controlling sorting of a second microparticle in the second group to not include the second microparticle in the mixture of microparticles in response to determining that the mixture of microparticles has a ratio of the first microparticle population to the second microparticle population within the range of constituent ratios.

[11] The microparticle sorting device of either [9] or [10], wherein controlling sorting of the first group of microparticles and the second group of microparticles further comprises: controlling sorting of a first microparticle in the first group to include the first microparticle in the mixture of microparticles in response to determining that the mixture of microparticles has a ratio of the first microparticle population to the second microparticle population outside the range of constituent ratios; and controlling sorting of a second microparticle in the second group to include the second microparticle in the mixture of microparticles in response to determining that the mixture of microparticles has a ratio of the first microparticle population to the second microparticle population outside the range of constituent ratios.

[12] The microparticle sorting device of any one of [1] to [11], wherein the at least one constituent amount is a constituent ratio of the first microparticle population to the second microparticle population.

[13] The microparticle sorting device of any one of [1] to [12], wherein the circuitry is further configured to set, based on the at least one constituent amount for the first microparticle population to the second microparticle population, a first number of microparticles to acquire for the first microparticle population and a second number of microparticles to acquire for the second microparticle population.

[14] The microparticle sorting device of [13], wherein controlling sorting of the first group of microparticles and the second group of microparticles further comprises: determining a third number of microparticles of the first microparticle population that has been sorted into the mixture of microparticles; controlling sorting of the first group of microparticles based on comparing the third number of microparticles to the first number of microparticles; determining a fourth number of microparticles of the second microparticle population that has been sorted into the mixture of microparticles; and controlling sorting of the second group of microparticles based on comparing the fourth number of microparticles to the second number of microparticles.

[15] The microparticle sorting device of [14], wherein controlling sorting of the first group of microparticles and the second group of microparticles further comprises: controlling sorting of a first microparticle in the first group to include the first microparticle in the mixture of microparticles in response to determining that the third number of microparticles is less than the first number of microparticles; and controlling sorting of a second microparticle in the second group to include the second microparticle in the mixture of microparticles in response to determining that the fourth number of microparticles is less than the second number of microparticles.

[16] The microparticle sorting device of either [14] or [15], wherein controlling sorting of the first group of microparticles and the second group of microparticles further comprises: controlling sorting of a first microparticle in the first group to not include the first microparticle in the mixture of microparticles in response to determining that the third number of microparticles equals or is greater than the first number of microparticles; and controlling sorting of a second microparticle in the second group to not include the second microparticle in the mixture of microparticles in response to determining that the fourth number of microparticles equals or is greater than the second number of microparticles.

[17] The microparticle sorting device of any one of [1] to [16], wherein the microparticles are cells and the mixture of microparticles is a mixture of cells including cells of a first cell type and cells of a second cell type.

[18] The microparticle sorting device of [17], wherein the cells are extracted from human blood.

[19] A method comprising: obtaining optical information indicating a first microparticle population and a second microparticle population; and controlling, based on at least one constituent amount for the first microparticle population and the second microparticle population, sorting of a first group of microparticles belonging to the first microparticle population and a second group of microparticles belonging to the second microparticle population to obtain a mixture of microparticles including microparticles both from the first microparticle population and the second microparticle population.

[20] The method of [19], wherein the microparticles are cells and the mixture of microparticles is a mixture of cells including cells of a first cell type and cells of a second cell type.

[21] The method of [20], further comprising administering the mixture of cells to a subject as a treatment for a medical condition or disease.

[22] The method of either [20] or [21], further comprising administering the mixture of cells to a subject as an immunotherapy treatment for a medical condition or disease.

[23] The method of any one of [20]-[22], further comprising extracting the cells from human blood.

[24] A cell therapeutic agent manufacturing device comprising circuitry configured to: obtain optical information indicating that a first group of cells is a first cell type and a second group of cells is a second cell type; and control, based on at least one constituent amount for the first cell type and the second cell type, sorting of the first group of cells and the second group of cells to obtain a mixture of cells including cells of the first cell type and cells of the second cell type.

[25] The cell therapeutic agent manufacturing device of [24], wherein the circuitry is further configured to control sorting of cells based on light from the cells detected in response to irradiating the cells with excitation light as the cells flow through a flow channel.

[26] The cell therapeutic agent manufacturing of [25], wherein the circuitry is further configured to determine, based on at least one characteristic of the detected light and the optical information, the first group of cells as being the first cell type and the second group of cells as being the second cell type.

[27] A microparticle sorting device including a determination unit that determines whether microparticles are sorted, on the basis of light generated by irradiating, with light, the microparticles flowing through a flow channel,
  in which the determination unit performs a primary sorting determination to determine, on the basis of characteristics of the light generated, whether the microparticles belong to any one of two or more different microparticle populations, and
  then performs a secondary sorting determination to determine whether the microparticles determined to belong to any one of the microparticle populations in the primary sorting determination are sorted, on the basis of the particle constituent ratio specified for the two or more different microparticle populations.

[28] The microparticle sorting device according to [27],
  in which the microparticle sorting device includes a sorting part that sorts microparticles determined to be sorted in the secondary sorting determination, and
  the microparticles sorted by the sorting part are collected in one container.

[29] The microparticle sorting device according to [28], in which the microparticles sorted by the sorting part are collected in one container, and the constituent ratio of the microparticles in the container is the specified particle constituent ratio, or falls within a specified numerical range including the specified particle constituent ratio.

[30] The microparticle sorting device according to [28], in which the microparticle sorting device includes one particle collection channel for collecting microparticles sorted by the sorting part into one container.

[31] The microparticle sorting device according to any one of [27] to [30], in which in the primary sorting determination, the determination unit determines whether a microparticle belongs to any one of the two or more different microparticle populations, based on whether the light generated by the light irradiation has a feature specified for fluorescence and/or scattered light.

[32] The microparticle sorting device according to any one of [27] to [31], in which the determination unit sets the number of acquired particles, on the basis of the specified particle constituent ratio.

[33] The microparticle sorting device according to any one of [27] to [32],
in which in the secondary sorting determination, the determination unit determines that the microparticles are sorted if the sorted number of microparticles determined to belong to any one of the two or more different microparticle populations in the primary sorting determination has not reached the number of acquired particles, set on the basis of the specified particle constituent ratio.

[34] The microparticle sorting device according to any one of [27] to [33],
in which in the secondary sorting determination, the determination unit determines that the microparticles are not sorted if the sorted number of microparticles determined to belong to any one of the two or more different microparticle populations in the primary sorting determination has reached the number of acquired particles, set on the basis of the specified particle constituent ratio.

[35] The microparticle sorting device according to any one of [27] to [34],
in which in the secondary sorting determination, the determination unit determines that the microparticles are sorted if the particle constituent ratio in the case of sorting the microparticles determined to belong to any one of the two or more different microparticle populations in the primary sorting determination falls within a specified numerical range including the specified particle constituent ratio.

[36] The microparticle sorting device according to any one of [27] to [35],
in which in the secondary sorting determination, the determination unit determines that the microparticles are not sorted if the particle constituent ratio in the case of sorting the microparticles determined to belong to any one of the two or more different microparticle populations in the primary sorting determination fails to fall within the specified numerical range including the specified particle constituent ratio.

[37] The microparticle sorting device according to any one of [27] to [36],
in which the microparticle sorting device includes a microchip for microparticle sorting, including a main flow channel through which a fluid including microparticles flows, a branched flow channel branched from the main flow channel, and a particle sorting flow channel that is coaxial with the main flow channel, and
the determination unit determines whether microparticles are sorted, on the basis of light generated by irradiating, with light, the microparticles in the fluid flowing in the microchip for microparticle sorting.

[38] The microparticle sorting device according to any one of [27] to [37], in which the microparticles are cells.

[39] The microparticle sorting device according to any one of [28] to [30],
in which the microparticles are cells,
cells determined to be sorted in the secondary sorting determination are collected in one container, and
the cells collected in the container are used as a drug.

[40] A cell therapeutic agent manufacturing device including:
a determination unit that determines whether cells are sorted, on the basis of light generated by irradiating, with light, the cells flowing through a flow channel; and
a cell sorting part that sorts cells determined to be sorted by the determination unit, in which the determination unit performs a primary sorting determination to determine, on the basis of characteristics of the light generated, whether the cells belong to any one of two or more different cell populations, and
then performs a secondary sorting determination to determine whether the cells determined to belong to any one of the cell populations in the primary sorting determination are sorted, on the basis of a cell constituent ratio specified for the two or more different cell populations, and
the cells sorted by the cell sorting part are collected in one container.

[41] A microparticle sorting method including a sorting determination step of determining whether microparticles are sorted, on the basis of light generated by irradiating, with light, the microparticles flowing through a flow channel,
in which the sorting determination step includes:
a primary sorting determination step of determining, on the basis of characteristics of the light generated, whether the microparticles belong to any one of two or more different microparticle populations; and
a secondary sorting determination step of determining, whether the microparticles determined to belong to any one of the microparticle populations in the primary sorting determination step are sorted, on the basis of a particle constituent ratio specified for the two or more different microparticle populations.

[42] A program for causing a microparticle sorting device or a cell therapeutic agent manufacturing device to execute a sorting determination step of determining whether microparticles are sorted on the basis of light generated by irradiating, with light, the microparticles flowing through a flow channel, the sorting determination step including:
a primary sorting determination step of determining, on the basis of characteristics of the light generated, whether the microparticles belong to any one of two or more different microparticle populations; and
a secondary sorting determination step of determining, whether the microparticles determined to belong to any one of the microparticle populations in the primary sorting determination step are sorted, on the basis of a particle constituent ratio specified for the two or more different microparticle populations.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

100 Microparticle sorting device
101 Light irradiation unit
102 Detection unit

103 Control unit
104 Signal processing unit
105 Determination unit
107 Sorting control unit
150 Microchip for microparticle sorting

The invention claimed is:

1. A microparticle sorting device comprising:
circuitry configured to:
obtain optical information indicating a first microparticle population and a second microparticle population; and
control, based on a predetermined range of constituent ratios of the first microparticle population to the second microparticle population, sorting of a first group of microparticles belonging to the first microparticle population and a second group of microparticles belonging to the second microparticle population to obtain a mixture of microparticles including microparticles both from the first microparticle population and the second microparticle population, wherein the sorting includes separating the first group of microparticles and the second group of microparticles from an input sample fluid containing microparticles, according to the predetermined range of constituent ratios, and directing the separated groups of microparticles into one container to obtain the mixture of microparticles.

2. The microparticle sorting device of claim 1, wherein the circuitry is further configured to control sorting of microparticles based on light from the microparticles detected in response to irradiating the microparticles with excitation light as the microparticles flow through a flow channel.

3. The microparticle sorting device of claim 2, wherein the circuitry is further configured to determine, based on at least one characteristic of the detected light and the optical information, the first group of microparticles as belonging in the first microparticle population and the second group of microparticles as belonging in the second microparticle population.

4. The microparticle sorting device of claim 3, wherein the at least one characteristic includes a feature of fluorescent light and/or scattered light.

5. The microparticle sorting device of claim 1, further comprising a microchip configured to perform the sorting of the first group of microparticles and the second group of microparticles.

6. The microparticle sorting device of claim 5, wherein the microchip comprises a particle collection channel configured to transport the mixture of microparticles into the container.

7. The microparticle sorting device of claim 6, wherein the microchip further comprises a main flow channel through which a fluid including microparticles of the first microparticle population and of the second microparticle population flows, and a branched flow channel connected to the main flow channel, wherein the particle collection channel is coaxial with the main flow channel.

8. The microparticle sorting device of claim 1, wherein controlling sorting of the first group of microparticles and the second group of microparticles further comprises:
controlling sorting of a first microparticle in the first group to not include the first microparticle in the mixture of microparticles in response to determining that the mixture of microparticles has a ratio of the first microparticle population to the second microparticle population within the predetermined range of constituent ratios; and
controlling sorting of a second microparticle in the second group to not include the second microparticle in the mixture of microparticles in response to determining that the mixture of microparticles has a ratio of the first microparticle population to the second microparticle population within the predetermined range of constituent ratios.

9. The microparticle sorting device of claim 1, wherein controlling sorting of the first group of microparticles and the second group of microparticles further comprises:
controlling sorting of a first microparticle in the first group to include the first microparticle in the mixture of microparticles in response to determining that the mixture of microparticles has a ratio of the first microparticle population to the second microparticle population outside the predetermined range of constituent ratios; and
controlling sorting of a second microparticle in the second group to include the second microparticle in the mixture of microparticles in response to determining that the mixture of microparticles has a ratio of the first microparticle population to the second microparticle population outside the predetermined range of constituent ratios.

10. The microparticle sorting device of claim 1, wherein the circuitry is further configured to set, based on the at least one constituent amount for the first microparticle population to the second microparticle population, a first number of microparticles to acquire for the first microparticle population and a second number of microparticles to acquire for the second microparticle population.

11. The microparticle sorting device of claim 10, wherein controlling sorting of the first group of microparticles and the second group of microparticles further comprises:
determining a third number of microparticles of the first microparticle population that has been sorted into the mixture of microparticles;
controlling sorting of the first group of microparticles based on comparing the third number of microparticles to the first number of microparticles;
determining a fourth number of microparticles of the second microparticle population that has been sorted into the mixture of microparticles; and
controlling sorting of the second group of microparticles based on comparing the fourth number of microparticles to the second number of microparticles.

12. The microparticle sorting device of claim 11, wherein controlling sorting of the first group of microparticles and the second group of microparticles further comprises:
controlling sorting of a first microparticle in the first group to include the first microparticle in the mixture of microparticles in response to determining that the third number of microparticles is less than the first number of microparticles; and
controlling sorting of a second microparticle in the second group to include the second microparticle in the mixture of microparticles in response to determining that the fourth number of microparticles is less than the second number of microparticles.

13. The microparticle sorting device of claim 11, wherein controlling sorting of the first group of microparticles and the second group of microparticles further comprises:
controlling sorting of a first microparticle in the first group to not include the first microparticle in the mixture of microparticles in response to determining that the third number of microparticles equals or is greater than the first number of microparticles; and controlling sorting of a second microparticle in the second group to not include the second microparticle in the mixture of microparticles in response to determining that the fourth number of microparticles equals or is greater than the second number of microparticles.

14. The microparticle sorting device of claim 1, wherein the microparticles are cells and the mixture of microparticles is a mixture of cells including cells of a first cell type and cells of a second cell type.

15. The microparticle sorting device of claim 14, wherein the cells are extracted from human blood.

16. A method comprising:
    obtaining optical information indicating a first microparticle population and a second microparticle population; and
    controlling, based on a predetermined range of constituent ratios of the first microparticle population to the second microparticle population, sorting of a first group of microparticles belonging to the first microparticle population and a second group of microparticles belonging to the second microparticle population to obtain a mixture of microparticles including microparticles both from the first microparticle population and the second microparticle population, wherein the sorting includes separating the first group of microparticles and the second group of microparticles from an input sample fluid containing microparticles, according to the predetermined range of constituent ratios, and directing the separated groups of microparticles into one container to obtain the mixture of microparticles.

17. The method of claim 16, wherein the microparticles are cells and the mixture of microparticles is a mixture of cells including cells of a first cell type and cells of a second cell type.

18. The method of claim 17, further comprising administering the mixture of cells to a subject as a treatment for a medical condition or disease.

19. The method of claim 17, further comprising administering the mixture of cells to a subject as an immunotherapy treatment for a medical condition or disease.

20. The method of claim 17, further comprising extracting the cells from human blood.

21. A cell therapeutic agent manufacturing device comprising:
    circuitry configured to:
    obtain optical information indicating that a first group of cells is a first cell type and a second group of cells is a second cell type; and
    control, based on a predetermined range of constituent ratios of the first cell type to the second cell type, sorting of the first group of cells and the second group of cells to obtain a mixture of cells including cells of the first cell type and cells of the second cell type, wherein the sorting includes separating the first group of microparticles and the second group of microparticles from an input sample fluid containing microparticles, according to the predetermined range of constituent ratios, and directing the separated groups of microparticles into one container to obtain the mixture of microparticles.

22. The cell therapeutic agent manufacturing device of claim 21, wherein the circuitry is further configured to control sorting of cells based on light from the cells detected in response to irradiating the cells with excitation light as the cells flow through a flow channel.

23. The cell therapeutic agent manufacturing of claim 22, wherein the circuitry is further configured to determine, based on at least one characteristic of the detected light and the optical information, the first group of cells as being the first cell type and the second group of cells as being the second cell type.

* * * * *